(12) United States Patent
Kleiner et al.

(10) Patent No.: US 12,048,637 B2
(45) Date of Patent: Jul. 30, 2024

(54) BONE GRAFT DELIVERY SYSTEM AND METHOD FOR USING SAME

(71) Applicant: Spinal Surgical Strategies, Inc., Incline Village, NV (US)

(72) Inventors: Jeffrey Kleiner, Denver, CO (US); Edward J. Grimberg, Jr., Golden, CO (US); Gregory Causey, Erie, CO (US); Alan Burkholder, Denver, CO (US)

( * ) Notice: Subject to any disclaimer, the term of this patent is extended or adjusted under 35 U.S.C. 154(b) by 0 days.

(21) Appl. No.: 18/218,810

(22) Filed: Jul. 6, 2023

(65) Prior Publication Data
US 2023/0355407 A1    Nov. 9, 2023

Related U.S. Application Data

(62) Division of application No. 17/770,987, filed as application No. PCT/US2020/050895 on Sep. 15, 2020, now Pat. No. 11,744,717.

(60) Provisional application No. 62/901,058, filed on Sep. 16, 2019, provisional application No. 62/900,960, filed on Sep. 16, 2019.

(51) Int. Cl.
| A61F 2/44 | (2006.01) |
| A61F 2/46 | (2006.01) |
| A61F 2/30 | (2006.01) |

(52) U.S. Cl.
CPC .......... *A61F 2/4601* (2013.01); *A61F 2/447* (2013.01); *A61F 2/4611* (2013.01); *A61F 2002/30593* (2013.01); *A61F 2002/3093* (2013.01); *A61F 2002/4627* (2013.01); *A61F 2002/4629* (2013.01)

(58) Field of Classification Search
CPC ...... A61F 2/4611; A61F 2/4601; A61F 2/447; A61F 2/44; A61F 2/4422
USPC ....... 623/17.11–17.16; 606/70–71, 280–299, 606/99–100
See application file for complete search history.

(56) References Cited

U.S. PATENT DOCUMENTS

| 5,015,247 | A | * | 5/1991 | Michelson | ............. | A61B 17/16 |
| | | | | | | 606/247 |
| 5,026,373 | A | * | 6/1991 | Ray | .................... | A61B 17/1637 |
| | | | | | | 606/279 |
| 5,458,638 | A | * | 10/1995 | Kuslich | .................. | A61F 2/446 |
| | | | | | | 606/907 |
| 5,683,394 | A | * | 11/1997 | Rinner | .................. | A61F 2/4455 |
| | | | | | | 606/279 |
| 6,129,763 | A | * | 10/2000 | Chauvin | ............... | A61F 2/4455 |
| | | | | | | 623/17.11 |

(Continued)

*Primary Examiner* — Jessica Weiss
(74) *Attorney, Agent, or Firm* — Corner Counsel, LLC

(57) ABSTRACT

The present disclosure relates to kits for bone graft delivery, and specifically, for near-simultaneous and integrated delivery of bone graft material during the placement of surgical cages or other medical implants in a patient's spine. The kits include integrated fusion cage and graft delivery devices that deliver and disperse biologic material through a fusion cage to a disc space and, that may, without withdrawal from the surgical site, allow for selectively detaching the fusion cage for deposit to the same disc space. The integrated fusion cage and graft delivery device is formed such that a hollow tube and plunger selectively and controllably place bone graft material and a fusion cage in or adjacent to the bone graft receiving area. The kits also include a cover plate that secures to the fusion cage.

16 Claims, 27 Drawing Sheets

(56) References Cited

U.S. PATENT DOCUMENTS

| | | | | |
|---|---|---|---|---|
| 6,206,922 | B1* | 3/2001 | Zdeblick | A61B 17/025 623/17.11 |
| 6,217,579 | B1* | 4/2001 | Koros | A61F 2/4455 623/17.11 |
| 7,235,105 | B2* | 6/2007 | Jackson | A61F 2/4611 623/17.16 |
| 7,621,938 | B2* | 11/2009 | Molz, IV | A61F 2/447 623/17.11 |
| 2002/0161444 | A1* | 10/2002 | Choi | A61F 2/446 623/17.11 |
| 2002/0169507 | A1* | 11/2002 | Malone | A61B 17/8685 623/17.11 |
| 2010/0234897 | A1 | 9/2010 | Fisher et al. | |
| 2012/0078371 | A1* | 3/2012 | Gamache | A61B 17/0682 623/17.16 |
| 2014/0074170 | A1* | 3/2014 | Mertens | A61F 2/4611 606/279 |
| 2015/0025635 | A1* | 1/2015 | Laubert | A61F 2/447 29/428 |
| 2019/0269521 | A1* | 9/2019 | Shoshtaev | A61F 2/4455 |

* cited by examiner

BONE GRAFT DELIVERY SYSTEM AND METHOD FOR USING SAME

RELATED APPLICATIONS

This application is a divisional of U.S. patent application Ser. No. 17/770,987, filed Apr. 21, 2022, issued as U.S. Pat. No. 11,744,717, as the U.S. National Phase of International Patent Application No. PCT/US20/50895, filed Sep. 15, 2020, which claims priority to U.S. Provisional Patent Application Ser. No. 62/901,058, filed Sep. 16, 2019 and U.S. Provisional Patent Application Ser. No. 62/900,960, filed Sep. 16, 2019. The disclosures of all of the foregoing applications are hereby incorporated by reference in their entireties.

FIELD OF THE INVENTION

This disclosure relates to orthopedic surgery, and more specifically to an apparatus and method for near-simultaneous and integrated delivery of bone graft material during the placement of surgical cages or other medical implants in a patient's spine.

BACKGROUND OF THE INVENTION

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances, a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is one that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, now U.S. Pat. No. 8,366,748, the entire disclosure of which is incorporated by reference in its entirety.

Vertebrectomy, or the removal or excision of a vertebra, is another type of spinal surgery that may be necessary to alleviate pain and/or correct spinal defects, such as when disc material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. Many of these products have similar handling characteristics and the literature reveals that they have similar healing prospects. They come in a syringe and it is up to the surgeon to apply the selected material to the target site. The most common site for application is to the disc space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

Autogenous bone (bone from the patient) or allograft bone (bone from another individual) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires extra surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or some caulking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device which jams the device and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device. Furthermore, the graft material is distributed only in the longitudinal axis and does not fill in the peripheral areas of the disc.

As mentioned, the method of delivery of bone graft to a particular location varies depending on the form of the bone graft utilized. For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"), the disclosure of which is incorporated herein by reference in its entirety. Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disc space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid-1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back, or through a direct lateral interbody fusion, or D-LIF, technique, involving placement of the cage through an incision in the side.

A typical procedure for inserting a common threaded and impacted fusion cage is as follows. First, the disc space between two vertebrae of the lumbar spine is opened using a wedge or other device on a first side of the vertebrae. The disc space is then prepared to receive a fusion cage. Conventionally, a threaded cage is inserted into the bore and the wedge is removed. A disc space at the first side of the vertebrae is then prepared, and a second threaded fusion cage inserted into the bore. Alternatively, the disc space between adjacent vertebrae may simply be cleared and a cage inserted therein. Often, only one cage is inserted obliquely into the disc space. Use of a threaded cage may be foregone in favor of a rectangular or pellet-shaped cage that is simply inserted into the disc space. Lastly, bone graft material may be inserted into the surgical area using separate tools and devices.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

Prior art bone graft delivery devices typically join a fusion cage to a delivery device with an interference fit, detents, or other similar systems. This can be problematic during various actions of the delivery system as unintentional release of the fusion cage can cause injury to the spine of the patient and/or reduce the likelihood of a successful surgery. In addition, prior art fusion cages dispense bone graft material within a disc space in a limited manner where bone graft material does not occupy the entire disc space.

SUMMARY OF THE INVENTION

Certain embodiments of the present disclosure relate to an apparatus and method for near-simultaneous and integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allows the biologic material to flow directly into and through the fusion cage and be dispersed within the disc space in a single step, and leave the detachable fusion cage in the surgical area. In one embodiment, the delivery assembly comprises multiple tubes that positively engage the fusion cage during positioning of the fusion cage, delivery of bone graft material, and installation of a cover plate to the fusion cage. Then, the delivery assembly releases the fusion cage at the conclusion of the surgical procedure. The multiple tube configuration reduces the likelihood of an unintentional release of the fusion cage. In addition, various embodiments of a fusion cage are described herein that more thoroughly dispense bone graft material within a disc space to increase the likelihood of a successful outcome for a patient.

By way of providing additional background, context, and to further satisfy the written description requirements of 35 U.S.C. § 112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. Pub. No. 2008/0255564 to Michelson.

By way of providing additional background, context, and to further satisfy the written description requirements of 35 U.S.C. § 112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. Pub. 2012/0022651 to Akyuz et al.; U.S. Pat. Appl. Pub. 2011/0015748 to Molz et al.; U.S. Pat. Appl. Pub. 2010/0249934 to Melkent; U.S. Pat. Appl. Pub. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. Pub. 2010/0198140 to Lawson; and U.S. Pat. Appl. Pub. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the following references are also incorporated by reference in their entireties for the purpose of explaining the nature of spinal fusion and devices and methods commonly associated therewith: U.S. Pat. No. D647,202 entitled "Bone Marrow Harvesting Device" to Seifert issued Oct. 18, 2011; U.S. Pat. No. 7,897,164 entitled "Compositions and Methods for Nucleus Pulposus Regeneration" to Scifert issued Mar. 1, 2011; U.S. Pat. Appl. Pub. No. 2010/0112029 entitled "Compositions and Methods for Nucleus Pulposus Regeneration" to Scifert issued May 6, 2010; U.S. Pat. Appl. Pub. No. 2010/0021518 entitled "Foam Carrier for Bone Grafting" to Scifert issued Jan. 28, 2010; U.S. Pat. No. 7,824,703 entitled "Medical Implants with Reservoir(s), and Materials Preparable From Same" to Scifert, et al., issued Nov. 2, 2010; U.S. Pat. Appl. Pub. No. 2006/0247791 entitled "Multi-Purpose Medical Implant Devices" to McKay, et al., issued Nov. 2, 2006; U.S. Pat. Appl. Pub. No. 2007/0225811 entitled "Conformable Orthopedic Implant" to Scifert, et al., issued Sep. 27, 2007; U.S. Pat. No. 6,746,487 entitled "Intramedullary Trial Fixation Device" to Scifert, et al., issued Jun. 9, 2004; U.S. Pat. Appl. Pub. No. 2013/0073041 entitled "Medical Implants With Reservoir(s), and Materials Preparable From Same" to Scifert et al., issued Mar. 21, 2013; U.S. Pat. Appl. Pub. No. 2010/0266689 entitled "Tissue Augmentation With Active Agent For Wound Healing" to Simonton et al., issued Oct. 21, 2010; U.S. Pat. Appl. Pub. No. 2011/0028393 entitled "Flowable Paste And Putty Bone Void Filler" to Vickers et al., issued Feb. 3, 2011; U.S. Pat. Appl. Pub. No. 2009/0099660 entitled "Instrumentation To Facilitate Access Into The Intervertebral Disc Space And Introduction Of Materials Therein" to Scifert issued Apr. 16, 2009; U.S. Pat. Appl. Pub. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; U.S. Pat. Appl. Pub. No. 2008/0260598 entitled "Devices, Methods and Systems for Hydrating a Medical Implant Material" to Gross et al., issued Oct. 23, 2008; U.S. Pat. Appl. Pub. No. 2007/0265632 entitled "Bone Cutting Template and Method of Treating Bone Fractures" to Seifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; U.S. Pat. Appl. Pub. No. 2007/0264300 entitled "Therapeutic Agent Carrier and Method of Treating Bone Fractures" to Scifert et al., issued Nov. 15, 2007; U.S. Pat. Appl. Pub. No. 2011/0020768 entitled "Implantable Screw and System for Socket Preservation" to Spagnoli et al., issued Jan. 27, 2011; U.S. Pat. Appl. Pub. No. 2012/0065687 entitled "Multi-Radius Vertebral Rod with a Varying Stiffness" to Ballard et al., issued Mar. 15, 2012; U.S. Pat. Appl. Pub. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; U.S. Pat. Appl. Pub. No. 2011/0160777 entitled "System and Methods of Maintaining Space for Augmentation of the Alveolar Ridge" to Spagnoli et al., issued Jun. 30, 2011; U.S. Pat. Appl. Pub. No. 2009/0246244 entitled "Malleable MultiComponent Implants and Materials Therefor" to McKay et al., issued Oct. 1, 2009; U.S. Pat. Appl. Pub. No. 2009/0246244 entitled "Malleable Multi-Component Implants and Materials Therefor" to McKay et al., issued Oct. 1, 2009; U.S. Pat. Appl. Pub. No. 2013/0110169 entitled "Vertebral Rod System and Methods of Use" to Hynes, et al., issued May 2, 2013; U.S. Pat. Appl. Pub. No. 2011/0184412 entitled "Pre-Assembled Construct With One Or More Non-Rotating Connectors For Insertion Into a Patient" to Scifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; U.S. Pat. Appl. Pub. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; U.S. Pat. Appl. Pub. No. 2010/0305575 entitled "Methods and Apparatus for Performing Knee Arthroplasty" to Wilkinson, et al., issued Dec. 2, 2010; U.S. Pat. Appl. Pub. No. 2011/0021427 entitled "Biphasic Calcium Phosphate Cement for Drug Delivery" to Amsden, et al., issued Jan. 27, 2011; U.S. Pat. Appl. Pub. No. 2012/0259335 entitled "Patello-Femoral Joint Implant and Instrumentation" to Scifert, et al., issued Oct. 11, 2012; U.S. Pat. Appl. No. 2011/0106162 entitled "Composite Connecting Elements for Spinal Stabilization Systems" to Ballard, et al., issued May 5, 2011; U.S. Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; U.S. Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; U.S. Pat. Appl. Pub. No. 2010/0331847 entitled "Methods and Apparatus for Performing Knee Arthroplasty" to Wilkinson, et al., issued Dec. 30, 2010; U.S. Pat. Appl. Pub. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

It is another aspect of the present disclosure to provide a fusion cage connection system for bone graft delivery, including a fusion cage having a distal end and a proximal end, the fusion cage having a first protrusion and a second protrusion positioned at the proximal end; an inserter tube having a first arm and a second arm, wherein the first arm and the second arm are each deflectable from an inward position to an outward position, wherein the first arm has a first protrusion and the second arm has a second protrusion, and wherein the first protrusion of the first arm interlocks with the first protrusion of the fusion cage and a second protrusion of the second arm interlocks with the second protrusion of the fusion cage when the first and second arms are in the outward positions, and the fusion cage is secured to the inserter tube; and a lock tube positioned within the inserter tube and movable relative to the inserter tube between a first position and a second position, wherein, in the first position, the lock tube prevents the first and second arms from deflecting to the inward positions to secure the fusion cage, and wherein, in the second position, the lock tube allows the first and second arms to deflect to the inward positions to release the fusion cage. The fusion cage connection system may further include a release tube position around the inserter tube and movable relative to the inserter tube between a first position and a second position, the inserter tube having at least one protrusion extending from an inner surface of the inserter tube, wherein, in the first position, the inserter tube allows the first and second arms to deflect to the outward positions to secure the fusion cage, and wherein, in the second position, the at least one protrusion drives at least one of the first arm and the second arm to the inward position to release the fusion cage.

It is another aspect of the present disclosure to provide a fusion cage connection system for bone graft delivery, including a fusion cage having a distal end and a proximal end, the fusion cage having a first protrusion and a second protrusion positioned at the proximal end; an inserter tube having a first arm and a second arm, wherein the first arm and the second arm are each deflectable from an inward position to an outward position, wherein the first arm has a first protrusion and the second arm has a second protrusion, and wherein the first protrusion of the first arm interlocks with the first protrusion of the fusion cage and a second protrusion of the second arm interlocks with the second protrusion of the fusion cage when the first and second arms are in the outward positions, and the fusion cage is secured to the inserter tube; and a release tube position around the inserter tube and movable relative to the inserter tube between a first position and a second position, the inserter tube having at least one protrusion extending from an inner surface of the inserter tube, wherein, in the first position, the inserter tube allows the first and second arms to deflect to the outward positions to secure the fusion cage, and wherein, in the second position, the at least one protrusion drives at least one of the first arm and the second arm to the inward position to release the fusion cage. The fusion cage connection system may further include a lock tube positioned within the inserter tube and movable relative to the inserter tube between a first position and a second position, wherein, in the first position, the lock tube prevents the first and second arms from deflecting to the inward positions to secure the fusion cage, and wherein, in the second position, the lock tube allows the first and second arms to deflect to the inward positions to release the fusion cage.

It is another aspect of the present disclosure to provide a fusion cage for bone graft delivery, including a top side and an opposing bottom side, the top side having at least one aperture that covers at least 10% of an area of the top side, and the bottom side having at least one aperture that covers at least 10% of an area of the bottom side; a left side and an opposing right side, the left side having at least one aperture that covers at least 80% of an area of the left side, and the right side having at least one aperture that covers at least 80% of an area of the right side; a ramp extending between the top and bottom sides, wherein a first face of the ramp extends from a centerline to the left side, and a second face of the ramp extends from the centerline to the right side; at least one top osseointegration area on the top side, wherein the at least one top osseointegration area has a plurality of protrusions and a plurality of depressions; and at least one bottom osseointegration area on the bottom side, wherein the at least one bottom osseointegration area has a plurality of protrusions and a plurality of depressions.

It is another aspect of the present disclosure to provide a delivery assembly for delivering bone graft, including a fusion cage having a protrusion; a lock tube extending along a longitudinal axis and defining a channel; an inserter tube positioned about the lock tube and extending along the longitudinal axis, the inserter tube having an arm deflectable between an inward position and an outward position, wherein a protrusion on the arm interlocks with the protrusion of the fusion cage when the arm is in the outward position, and the lock tube prevents the arm from defecting to the inward position; and a release tube positioned about the inserter tube and extending along the longitudinal axis, the release tube having a protrusion extending from an inner surface of the release tube into a depression in the inserter tube, wherein the release tube is configured to move relative to the inserter tube along the longitudinal axis, and the protrusion moves out of the depression to drive the arm to the inward position and release the fusion cage from the inserter tube.

It is one aspect of the present disclosure to provide a bone graft material delivery system that positively secures and releases a fusion cage from a delivery assembly to prevent inadvertent release of the fusion cage, which cage injure the patient and decrease the likelihood of success of a surgery. As described in further detail below, a series of tubes can ensure that a delivery assembly has a positive hold on the fusion cage and a definitive release of the fusion cage at the conclusion of the procedure.

It is a further aspect of the present disclosure to provide a fusion cage for a bone graft delivery system that distributes bone graft material in one or more preferred directions within a disc space. As described in further detail below, a fusion cage can have a ramp and apertures of various sizes and relative arrangements that deliver gone graft materials in particular directions and in particular proportions.

In another embodiment for the integrated fusion cage and graft delivery device, the detachable fusion cage is detachable by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment for the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion 30 cage and graft delivery device: U.S. Patent Appl. No. 2009/0187194 to Hamada.

In another embodiment for the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively, or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite;

an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment for the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. Plasma Phys., 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 Polymeric Materials Encyclopedia 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. Patent Application is incorporated herein by reference in order to provide an illustrative and enabling disclosure and general description of means to selectably detach the fusion cage of the integrated fusion cage and graft delivery device: U.S. Pat. No. 7,749,555 to Zanella et al.

In one embodiment, the device is not a caulking gun style device, that is the bone graft material and/or the fusion cage are not delivered and/or positioned using a hand-pump and/or hand-squeeze mechanism. Instead, the device delivers graft material and/or a fusion cage using a hollow tube and plunger arrangement which is not a caulking gun style device and further, does not appreciably disrupt or block the user's view of the surgical site and/or enable precision delivery of bone graft material and/or a fusion cage to the surgical site. Indeed, the device of one embodiment of the present disclosure is distinctly unlike the caulking gun device of U.S. Pat. Appl. No. 2004/0215201 to Lieberman ("Lieberman"), which requires an L-shaped base member handle, rack teeth to advance a plunger member, and user action on a lever of the Lshaped base member handle to deploy bone graft material. In one embodiment, the device of this application is not a caulking gun style device and does not comprise rack teeth, a base member handle and at least one component that obscures user viewing of the surgical site. Lieberman is incorporated by reference in its entirety for all purposes.

Similarly, in one embodiment, the device is distinctly unlike the caulking gun device of U.S. Pat. Appl. No. 2002/0049448 to Sand et al ("Sand"), which requires a gun and trigger mechanism in which the user squeezes together a gun-style handle to deploy material into bone. The Sand device obstructs the view of the user of the delivery site. In one embodiment, the device of this application is not a caulking gun style device and does not comprise an opposing-levered, gun-style delivery mechanism and at least one component that obscures user viewing of the surgical site. Sand is incorporated by reference in its entirety for all purposes.

Other caulking gun type devices are described in U.S. Pat. Nos. 8,932,295 and 9,655,748 which are each incorporated herein by reference in their entirety.

However, while in some embodiments the bone graft delivery device of the present disclosure may not be a caulking gun-style device, it is to be expressly understood that caulking gun-type designs are within the scope of the present disclosure, and indeed may even be desirable in certain embodiments and applications. By way of non-limiting example, it may be advantageous to provide a caulking gun-type mechanism for the purpose of making it easier for a user to apply pressure against a plunger to facilitate controlled movement of the plunger and/or a hollow tube relative to the plunger. A handle and pivotally mounted trigger attached to a ratchet-type push bar, as are commonly associated with caulking guns and similar devices, may be provided, in these and other embodiments, instead of or in addition to a rack-and-pinion-type linear actuator.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl. No. 2007/0185496 to Beckman et al ("Beckman"), U.S. Pat. Appl. No. 2009/0275995 to Truckai et al ("Truckai") and U.S. Pat. Appl. No. 2006/0264964 to Scifert et al ("Seifert"). Krueger, Beyar, Beckman, Truckai and Seifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("PerezCruet"). Further, the fusion device of this application features a distal tip that functions to precisely position the fusion device and stabilize the device during delivery of bone graft material. Perez-Cruet is incorporated by reference in its entirety for all purposes.

In one embodiment of an intervertebral implant system, the system includes an implant having a top wall, a bottom wall opposite the top wall, and a plurality of sidewalls extending between the top and bottom walls to define an interior space, wherein at least one of the plurality of sidewalls has a delivery opening that is continuous with the interior space, such that the at least one of the plurality of sidewalls defines inside borders of the delivery opening; and a cover plate configured to be secured to the at least one of the plurality of sidewalls, the cover plate including an exterior surface and an interior surface opposite the exterior surface. The interior surface includes a rotating wedge and tabs that are operably connected to the rotating wedge, whereby rotation of the rotating wedge causes the tabs to extend outwardly and securely engage the inside borders of the delivery opening to secure the cover plate to the at least one of the plurality of sidewalls.

In another embodiment of an implant delivery system having a cage-like implant with at least one sidewall having a delivery opening with borders defined by the at least one sidewall, a cover plate is provided and configured to be secured to the at least one sidewall. The cover plate includes an exterior surface and an interior surface opposite the exterior surface and having a rotating wedge and tabs that are operably connected to the rotating wedge, whereby rotation of the rotating wedge causes the tabs to extend outwardly and securely engage the inside borders of the delivery opening to secure the cover plate to the at least one sidewall.

In one embodiment of a cover plate installation system for a fusion cage, the system includes a fusion cage having a distal end and a proximal end, the fusion cage having a protrusion positioned at the proximal end; an inserter including a rod extending in a longitudinal direction, the rod having a tip at a first end and a first sleeve at a second end, and a sheath positioned about the rod and extending in the longitudinal direction, the sheath having a threaded first end and a second sleeve at a second end; and a cover plate. The cover plate includes a body having a threaded aperture that receives the threaded first end of the sheath, wherein the second sleeve can rotate the sheath to release the sheath and the inserter from the cover plate, a wedge that is rotatable relative to the body, where the tip of the rod is operably engaged to the wedge to rotate the wedge, and a tab that is deflectable from an inward position to an outward position where the tab engages the protrusion of the fusion cage to secure the cover plate to the fusion cage, wherein, in a first position, the wedge allows the tab to remain in the inward position, and wherein, in a second position, the first sleeve rotates the wedge to push the tab into the outward position and secure the cover plate to the fusion cage.

In one embodiment of a method for delivering an intervertebral implant, the method incudes positioning an intervertebral implant within an intervertebral space; removeably engaging a cover plate to a distal end of an inserter; extending the cover plate and inserter through a channel in an inserter tube, so as to position the cover plate and inserter tube within the intervertebral space; contacting the cover plate to a portion of the intervertebral implant; manipulating a portion of the inserter tube to secure the cover plate to the portion of the intervertebral implant; releasing the inserter tube from the cover plate; and removing the inserter tube from the intervertebral space.

In one embodiment of a method for implanting a fusion cage implant having a top wall, a bottom wall opposite the top wall, and a plurality of sidewalls extending between the top and bottom walls to define an interior space, at least one of the plurality of sidewalls having a delivery opening that is continuous with the interior space, such that the at least one of the plurality of sidewalls defines inside borders of the delivery opening, and a cover plate configured to be secured to the at least one of the plurality of sidewalls, the cover plate including a rotatable wedge and tabs that are operably connected to the rotatable wedge, the method includes positioning the fusion cage implant within an intervertebral space; removeably engaging the cover plate to a distal end of an inserter; extending the cover plate and inserter through a channel in an inserter tube, so as to position the cover plate and inserter within the intervertebral space; contacting the cover plate to the delivery opening of the fusion cage implant; and manipulating a portion of the inserter tube to rotate the rotatable wedge and thereby cause the tabs to extend outwardly and securely engage the inside borders of the delivery opening to secure the cover plate to the at least one of the plurality of sidewalls, and thereby cover the delivery opening.

In one embodiment of a kit for bone graft delivery, the kit includes an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening. The kit further includes a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge. The kit also includes an inserter tube having a rod configured to rotatably engage the rotating wedge and move the tabs so as to secure the cover plate to the at least one of the plurality of sidewalls to cover the delivery opening.

In another embodiment of a kit for bone graft delivery, the kit includes an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening. The kit further includes a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge.

In still another embodiment of a kit for bone graft delivery, the kit includes a an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening. The kit further includes a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge. The kit also includes an inserter tube having a rod configured to rotatably engage the rotating wedge and move the tabs so as to secure the cover plate to the at least one of the plurality of sidewalls to cover the delivery opening. The cover plate is configured to be entirely contained within the delivery opening of the implant, whereby rotation of the rotating wedge causes the tabs to extend outwardly and securely engage the inside borders of the delivery opening to secure the cover plate to the first sidewall. The first sidewall includes first and second protrusions and each of the tabs includes a recess configured to receive a respective one of the first and second protrusions therein, to thereby secure the cover plate to the first sidewall.

In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771,473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez; U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 2010/0286779 to Thibodean; U.S. Patent Application Publication No. 2011/0301712 to Palmatier; U.S. Patent Application Publication No. 2012/0022603 to Kirschman; U.S. Patent Application Publication No. 2012/0035729 to Glerum; U.S. Patent Application Publication No. 2012/0089185 to Gabelberger; U.S. Patent Application Publication No. 2012/0123546 to Medina; U.S. Patent Application Publication No. 2012/0197311 to Kirschman; U.S. Patent Application Publication No. 2012/0215316 to Mohr; U.S. Patent Application Publication No. 2013/0158664 to Palmatier; U.S. Patent Application Publication No. 2013/0178940; U.S. Patent Application Publication No. 2014/0012383 to Triplett; U.S. Patent Application Publication No. 2014/0156006; U.S. Patent Application Publication No. 2014/0172103 to O'Neil; U.S. Patent Application Publication No. 2014/0172106 to To; U.S. Patent Application Publication No. 2014/0207239 to Barreiro; U.S. Patent Application Publication No. 2014/0228955 to Weiman; U.S. Patent Application Publication No. 2014/0236296 to Wagner; U.S. Patent Application Publication No. 2014/0236297 to Iott; U.S. Patent Application Publication No. 2014/0236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to Perez-Cruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 2014/0257405; U.S. Patent Application Publication No. 2014/0257490 to Himmelberger et al.; U.S. Pat. No. 8,828,019 to Raymond et al.; U.S. Patent Application Publication No. 2014/0288652 to Boehm et al.; U.S. Patent Application Publication No. 2014/0287055 to Kunjachan; U.S. Patent Application Publication No. 2014/0276896 to Harper; U.S. Patent Application Publication No. 2014/0277497 to Bennett et al.; U.S. Patent Application Publication No. 2012/0029635 to Schoenhoeffer et al.; U.S. Patent Application Publication No. 2014/0303675 to Mishra; U.S. Patent Application Publication No. 2014/0303731 to Glerum; U.S. Patent Application Publication No. 2014/0303732 to Rhoda et al.; U.S. Pat. No. 8,852,279 to Weiman; PCT Pub. WO 2012/031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 2014/0296985 to Balasubramanian et al.; U.S. Patent Application Publication No. 2014/0309268 to Arnou; U.S. Patent Application Publication No. 2014/0309548 to Merz et al.; U.S. Patent Application Publication No. 2014/0309697 to Iott et al.; U.S. Patent Application Publication No. 2014/0309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 2011/0208226 to Fatone et al.; U.S. Patent Application Publication No. 2010/0114147 to Biyani; U.S. Patent Application Publication No. 2011/0144687 to Kleiner; U.S. Pat. No. 8,852,243 to Morgenstern Lopez et al.; U.S. Pat. No. 8,597,333 to Morgenstern Lopez et al.; U.S. Pat. No. 8,518,087 to Lopez et al.; U.S. Patent Application Publication No. 2012/0071981 to Farley et al.; U.S. Patent Application Publication No. 2013/0006366 to Farley et al.; U.S. Patent Application Publication No. 2012/0065613 to Pepper et al.; U.S. Patent Application Publication No. 2013/0006365 to Pepper et al.; U.S. Patent Application Publication No. 2011/0257478 to Kleiner et al.; U.S. Patent Application Publication No. 2009/0182429 to Humphreys et al.; U.S. Patent Application Publication No. 2005/0118550 to Turri; U.S. Patent Application Publication No. 2009/0292361 to Lopez; U.S. Patent Application Publication No. 2011/0054538 to Zehavi et al.; U.S. Patent Application Publication No. 2005/0080443 to Fallin et al.; U.S. Pat. No. 8,778,025 to Ragab et al.; U.S. Pat. No. 8,628,576 to Triplett et al; U.S. Pat. No. 8,808,304 to Weiman, and U.S. Pat. No. 8,828,019 to Raymond.

All of the following U.S. Patents are also incorporated herein by reference in their entirety: U.S. Pat. Nos. 6,595,998; 6,997,929; 7,311,713; 7,749,255; 7,753,912; 7,780,734; 7,799,034; 7,875,078; 7,931,688; 7,967,867; 8,075,623; 8,123,755; 8,142,437; 8,162,990; 8,167,887; 8,197,544; 8,202,274; 8,206,395; 8,206,398; 8,317,802; 8,337,531; 8,337,532; 8,337,562; 8,343,193; 8,349,014; 8,372,120; 8,394,108; 8,414,622; 8,430,885; 8,439,929; 8,454,664; 8,475,500; 8,512,383; 8,523,906; 8,529,627; 8,535,353; 8,562,654; 8,574,299; 8,641,739; 8,657,826; 8,663,281; 8,715,351; 8,727,975; 8,828,019; 8,845,640; 8,864,830; 8,900,313; 8,920,507; 8,974,464; 9,039,767; 9,084,686; 9,095,446; 9,095,447; 9,101,488; 9,107,766; 9,113,962; 9,114,026; 9,149,302; 9,174,147; 9,216,094; 9,226,777; 9,295,500; 9,358,134; 9,381,094; 9,439,692; 9,439,783; 9,445,921; 9,456,830; 9,480,578; 9,498,200; 9,498,347; 9,498,351; 9,517,140; 9,517,141; 9,517,142; 9,545,250; 9,545,279; 9,545,313; 9,545,318; 9,610,175; 9,629,668; 9,655,660; 9,655,743; 9,681,889; 9,687,360; 9,707,094; 9,763,700; 9,861,395; 9,980,737; 9,629,729; U.S. Pat. Pub. 9,993,353; U.S. Pat. Pub. 2014/0088712; U.S. Pat. Pub. 2014/0276581; U.S. Pat. Pub. 2014/0371721; U.S. Pat. Pub. 2016/0296344; U.S. Pat. Pub. 2017/0367846; U.S. Pat. Pub. 2017/0354514.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the disclosure.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 1A:
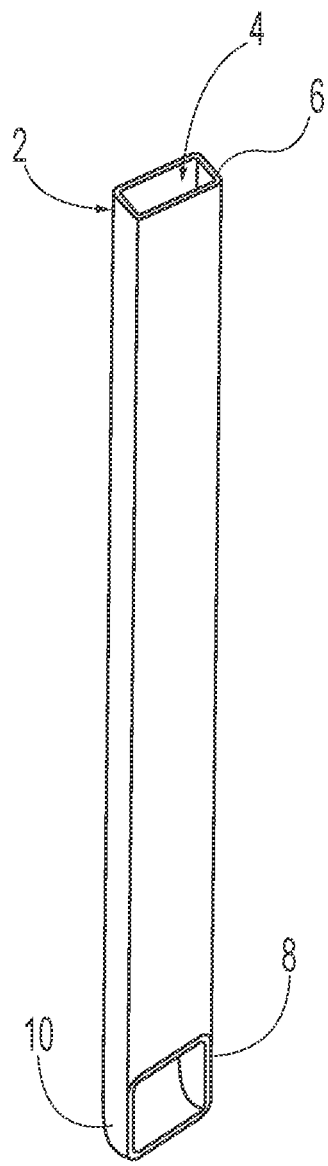
FIG. 1A is a front perspective view of a hollow tubular member of the device for delivering bone graft.

To provide further clarity to the Detailed Description provided herein in the associated drawings, the following list of components and associated numbering are provided as follows:

| Reference No. | Component |
|---|---|
| 2 | Hollow tube |
| 4 | Opening (of Hollow tube) |
| 6 | First (or proximal) end (of Hollow tube) |
| 8 | Second (or distal) end (of Hollow tube) |
| 10 | Curved surface (of Hollow tube) |
| 12 | Plunger |
| 16 | Handle (of Plunger) |
| 18 | Second (or distal) end (of Plunger) |
| 19 | Horizontal surface (of Plunger) |
| 20 | Curved surface (of Plunger) |
| 50 | Wedge-shaped Second end (of Hollow tube) |
| 52 | Wedge-shaped Second end (of Plunger) |
| A | Height of Opening (in Hollow tube) |
| B | Width of Opening (in Hollow tube) |
| 100 | Delivery Assembly |
| 102 | Fusion Cage |
| 104 | Release Tube |
| 106 | Release Collar |
| 108 | Inserter Collar |
| 110 | Lock Collar |
| 112 | Impactor |
| 114 | Inserter |
| 116 | Cover Plate |
| 117 | Channel |
| 118 | Head |
| 120 | Sleeve |
| 122 | Recess |
| 124 | Distal End |
| 126 | Stud |
| 128 | Channel |
| 130 | Inserter Tube |
| 132 | Lock Tube |
| 134 | Funnel |
| 136 | Plunger |
| 138 | Pliers |
| 140 | First Sleeve |
| 142 | Second Sleeve |
| 144 | Protrusion |

-continued

| Reference No. | Component |
|---|---|
| 145 | Body |
| 146 | Tab |
| 147 | Recess |
| 148 | Wedge |
| 149 | Protrusion |
| 150 | Rod |
| 151 | Recess |
| 152 | First Sheath |
| 154 | Second Sheath |
| 156 | First Arm |
| 158 | Second Arm |
| 160 | Protrusion |
| 162 | Tab |
| 163 | Protrusion |
| 164 | Spine |
| 166 | Recess |
| 168 | Protrusion |
| 169 | Aperture |
| 170 | Protrusion |
| 172 | Body |
| 174 | Top Side |
| 176 | Bottom Side |
| 178 | Left Side |
| 180 | Right Side |
| 182 | Ramp |
| 184 | Retrieval Aperture |
| 186 | Forward Aperture |
| 188 | Side Aperture |
| 190 | Top Aperture |
| 192 | Enhanced Surface |

DETAILED DESCRIPTION

The present disclosure relates to a device and method for integrated and near-simultaneous delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device or delivery assembly is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present disclosure also contemplates the delivery of bone graft material and/or a fusion cage with or without the use of a plunger, and with or without the use of various other tools and devices described in greater detail herein.

Referring now to FIG. 1A, an exemplary integrated fusion cage and graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape, or those that are approximately rectangular and have rounded corners or edges, or those with at least one defined angle to include obtuse, acute, and right angles can provide a shape in some situations that is more congruent with the size or shape of the annulotomy of a particular disc space.

Figure 1B:
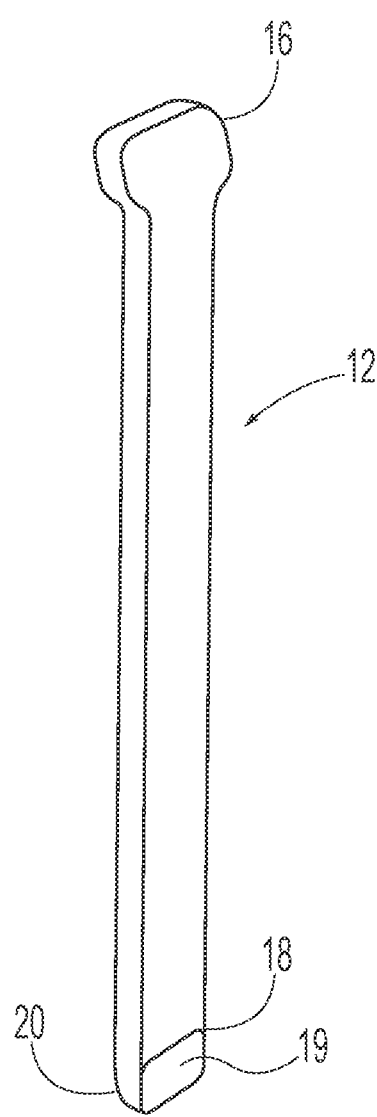
FIG. 1B is a front perspective view of the plunger of the device in FIG. 1A.

Referring now to FIG. 1B, a plunger 12 is shown for use with the hollow tube 2 of FIG. 1A. The plunger 12 is generally of the same geometry as the hollow portion of the hollow tube 2, extending at least the same length of hollow tube 2. The plunger 12 may include, as depicted in FIG. 1B, at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to affect the substantial removal of all of the bone graft material placed into the hollow tube; more specifically, any shape that allows conformance between the internal contour of the distal end of the hollow tube and the distal end of the plunger will affect the substantial removal of the bone graft material.

Figure 1C:
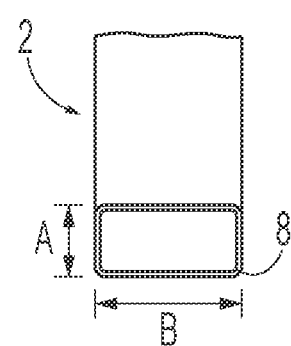
FIG. 1C is a cross sectional view of a portion of the device in FIG. 1A.

In the embodiment, of FIG. 1A-C, a contoured leading edge is provided on the plunger 12 to correspond with the internal contour of distal end 8 of the hollow tube 2 of the delivery device. This contoured plunger serves several purposes: First, it maintains the plunger in a desirable rotational position with respect to the hollow tube (i.e., prevents the plunger from inadvertently or intentionally being manipulated to rotate about the longitudinal axis of the hollow tube). Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12.

According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present disclosure, so long as that the opening at 30 the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a user's hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Figure 2:
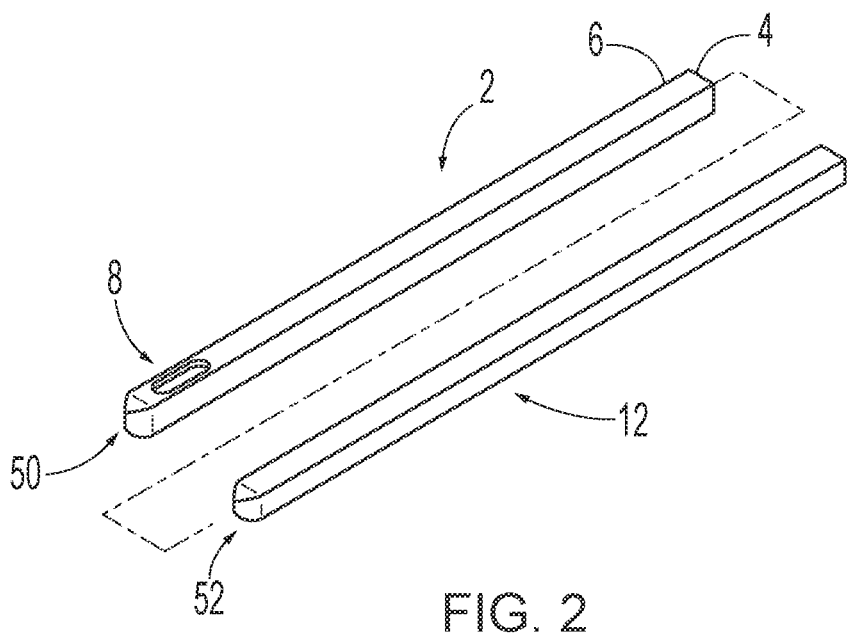
FIG. 2 is a front perspective view of one embodiment of the device, showing the relationship between the tubular and plunger portions where the tubular portion includes two lateral facing openings at the distal end of the tubular portion and a wedge-shaped distal end of the tubular member.

Referring now to FIGS. 2-6D, a preferred embodiment of the device is shown. In regard to FIG. 2, an integrated fusion cage and graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 3). Also in FIG. 2, the plunger member 12 is shown. The manner of insertion of plunger member 12 into tubular member 2 is also provided. Thus, as shown in FIG. 2, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore, regarding FIG. 2, a preferred embodiment of the distal end 8 of the tubular member 2 and the distal end 18 of the plunger member 12 is provided. The configuration provided, a wedge-shaped end 50 of the tubular member 2 and a wedge-shaped end 52 of the plunger 12, allows substantially all of the bone graft material to be removed and thus inserted into the surgical area when the plunger 12 is fully inserted into the tubular member 2. The wedge-shaped feature 50 of the distal end 8 of the tubular member 2 and the wedge-shaped end 52 of the distal end 18 of the plunger member 12 is discussed in additional detail with respect to FIGS. 4 and 5 below. The ability to remove substantially all of the bone graft material is an important feature of the disclosure because bone graft material is traditionally expensive and may require surgery to obtain.

Figure 3:
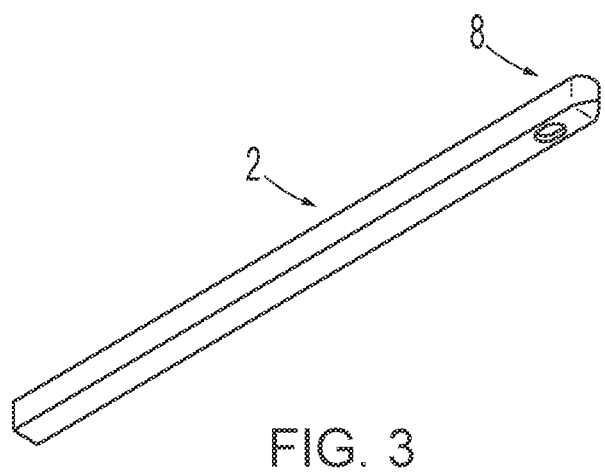
FIG. 3 is another front perspective view of the tubular portion of the device of FIG. 2 showing the second of two lateral openings at the distal end of the tubular portion and a wedge-shaped distal end of the tubular member.

Referring now to FIG. 3, a perspective view of a preferred embodiment of the hollow tubular member 2 is provided. Consistent with FIG. 2, the generally hollow tube 2 is shown with one of two lateral openings at the distal end 8 of the tubular member 2 viewable (the other is viewable in FIG. 2). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular), and/or one or more lateral openings may comprise a first pair of edges and a second pair of edges, wherein the first pair of edges are straight and the second pair of edges are not straight.

Figure 4:
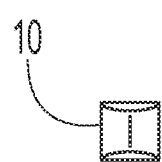
FIG. 4 is a front elevation view of the distal end of the tubular portion of the device of FIG. 2.

Referring now to FIG. 4, an elevation view of the wedge-shaped distal end 50 of the tubular member 2 is provided. In this embodiment, the distal end 52 of the plunger 12 would conform to the same shape, to allow close fitting of the plunger and the hollow tubular member. This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger 12 need not terminate in a wedge-shape surface 52 to affect the substantial removal of all of the bone graft material placed into the hollow tube 2; more specifically, any shape that allows conformance between the internal contour of the distal end of the hollow tube and the distal end of the plunger will affect the substantial removal of the bone graft material.

Figure 5:
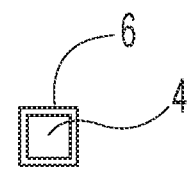
FIG. 5 is a bottom elevation view of the proximal end of the tubular device of FIG. 2.

Referring now to FIG. 5, an elevation view of the opening 4 of the proximal end 6 of the hollow tubular member 2 is provided. As shown in FIG. 5, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtuse, acute, and right angles can provide a shape in some situations that is more congruent with the size or shape of the annulotomy of a particular disc space.

Figure 6A:
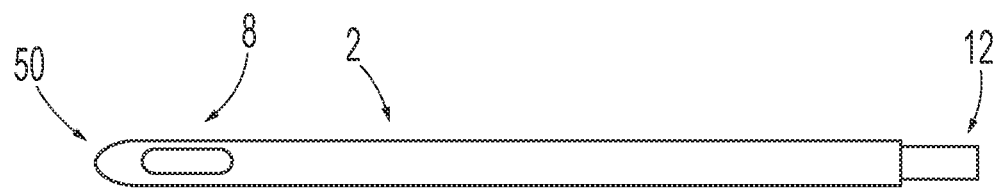
FIG. 6A is a top plan view of the device of FIG. 2 with the plunger portion fully inserted into the tubular portion.
Figure 6B:
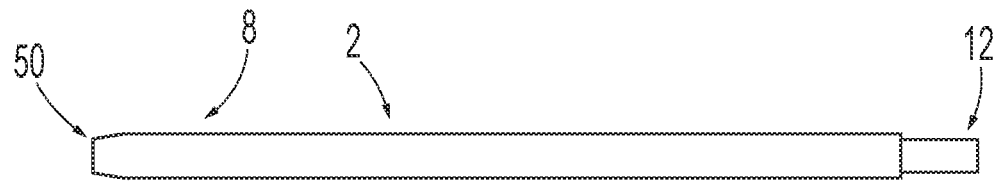
FIG. 6B is a left elevation view of the device of FIG. 2 with the plunger portion fully inserted into the tubular portion.
Figure 6C:
FIG. 6C is a bottom plan view of the device of FIG. 2 with the plunger portion fully inserted into the tubular portion.
Figure 6D:
FIG. 6D is a right elevation view of the device of FIG. 2 with the plunger portion fully inserted into the tubular portion.

Referring to FIGS. 6A-6D, sequential elevation views of the square-shaped embodiment of the integrated fusion cage and graft delivery device are provided, depicting the complete insertion of the plunger 12 into the hollow tubular member 2. In each of FIGS. 6A-6D, the wedge-shaped distal end 50 of the tubular member 2 is depicted. Also, each of FIGS. 6A-6D depict the additional length of the plunger element 12 when inserted into the tubular member 2. FIG. 6A shows one of two lateral openings at the distal end 8 of the hollow tubular member 2. FIG. 6C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Figure 7A:
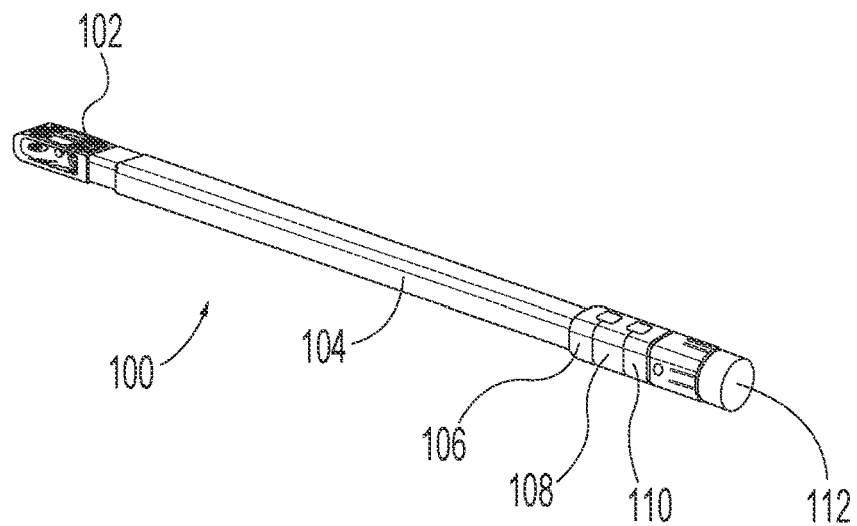
FIG. 7A is a perspective view of various components of a delivery assembly.
Figure 7B:
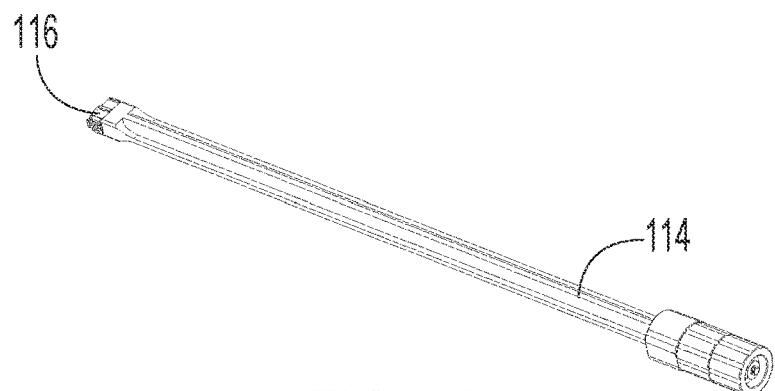
FIG. 7B is a perspective view of an inserter and a cover plate.
Figure 7C:
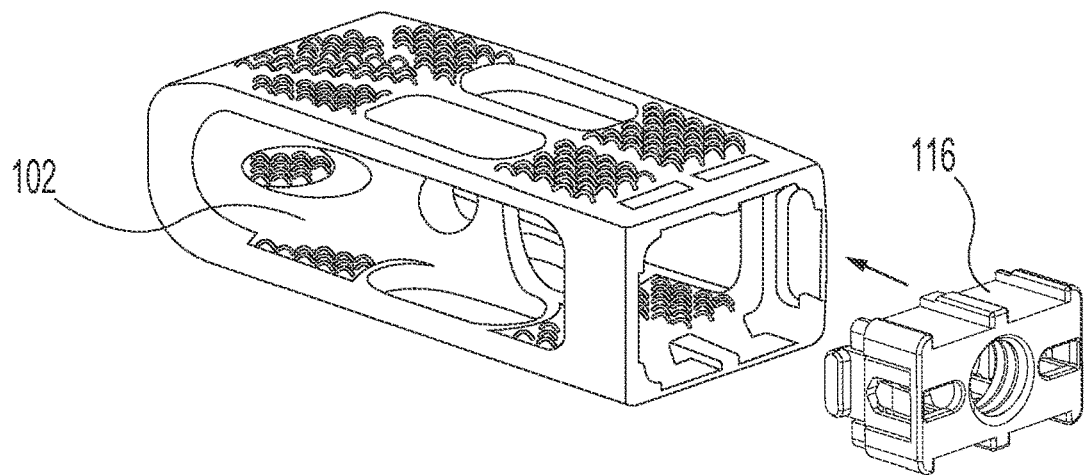
FIG. 7C is a perspective view of a fusion cage and a cover plate.

Referring to FIGS. 7A-7C, perspective views of a delivery assembly 100, an inserter 114, a fusion cage 102, and a cover plate 116 are provided. These devices and components allow for the positioning of the fusion cage 102 in a disc space within a spinal column, delivery of bone graft material to the disc space, positioning of the cover plate 116 in the fusion cage 102, and release of the delivery assembly 100 from the fusion cage 102. The term "delivery assembly" can generally refer to the entire system described herein, and can also refer to the assembly of nested tubes that are selectively connected to the fusion cage and receive an impactor 112, bone graft material, the inserter 114, etc. In addition, it will be appreciated that embodiments described in the present disclosure can be used with other devices besides a fusion cage 102. For instance, the delivery assemblies 100 described herein can be used with other ends such as those described in PCT App. No. PCT/US19/29447 and/or U.S. Prov. App. No. 62/900,814, which are incorporated herein by reference in their entireties.

Figure 39:
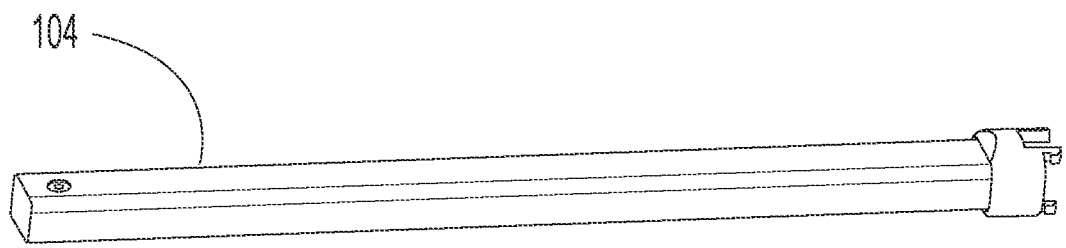
FIG. 39 is a perspective view of a release tube.

The delivery assembly 100 in FIG. 7A comprises a lock tube, an inserter tube positioned about the lock tube, and a release tube 104 positioned about the inserter tube (also see FIG. 39). These tubes selectively secure the fusion cage 102 for positioning in the disc space, delivery of bone graft material, and positioning of the cover plate 116, and then the tubes release the fusion cage at the conclusion of the procedure so that the fusion cage and the bone graft material remain in the disc space. A release collar 106 is positioned at a proximal end of the release tube 104. Though the inserter and lock tubes are partially shown or not shown, an inserter collar 108 of the inserter tube and a lock collar 110 of the lock tube are shown in FIG. 7A. These collars 108, 110 are positioned at the proximal ends of the respective tubes. Moreover, pliers can engage the collars 106, 108, 110 to move tubes relative to each other along a longitudinal axis of the delivery assembly 100. For example, pliers can separate the lock collar 110 from the inserter collar 108 to remove the lock tube from the inserter tube, and pliers can separate the inserter collar 108 from the release collar 106 to remove the inserter tube from the release tube.

In FIG. 7A, an impactor 112 extends through the tubes and directly engages the fusion cage 102 so that a hammer or other device can strike the impactor 112 and position the fusion cage 102 in a disc space without affecting the other components of the delivery assembly 100. FIG. 7B depicts an inserter 114 that has a cover plate 116 positioned on a distal end of the inserter 114. After bone graft material has been driven through the delivery assembly 100, through the fusion cage 102, and into the disc space, the cover plate 116 is applied to (see FIG. 7C) and seals the fusion cage 102 to retain the bone graft material in the disc space. As described in detail below, the inserter 114 is both selectively engaged to the cover plate 116 and can actuate features of the cover plate 116 to secure the cover plate 116 to the fusion cage 102.

Figure 8:
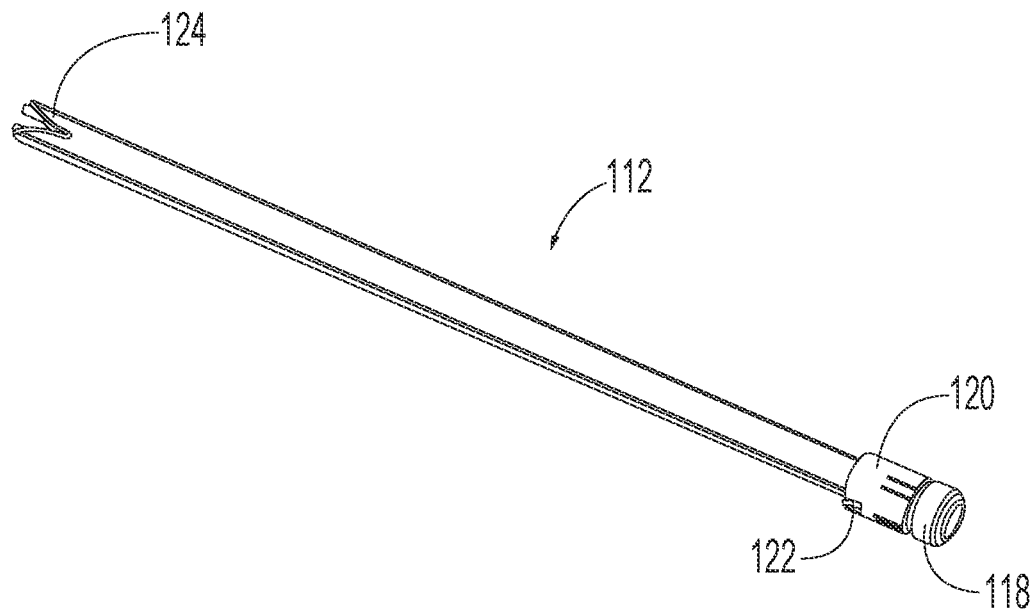
FIG. 8 is a perspective view of an impactor with a head, a sleeve, and a distal end.

Referring to FIG. 8, a perspective view of an impactor 112 is provided. The impactor 112 extends along a longitudinal axis with a head 118 positioned at a proximal end. The head 118 is the location where a hammer or other device can strike the impactor 112 to position the fusion cage in the disc space. A sleeve 120 is positioned adjacent to the head 118, and the sleeve of the impactor 112 defines a recess 122 that selectively engages a stud of the lock collar in lug type of connection. The selective engagement prevents an unintentional release of the impactor 112 from the delivery assembly as a device strikes the impactor 112. A distal end 124 of the impactor 112 engages the fusion cage 102 to directly transmit force from a striking device to the fusion cage 102.

Figure 9:
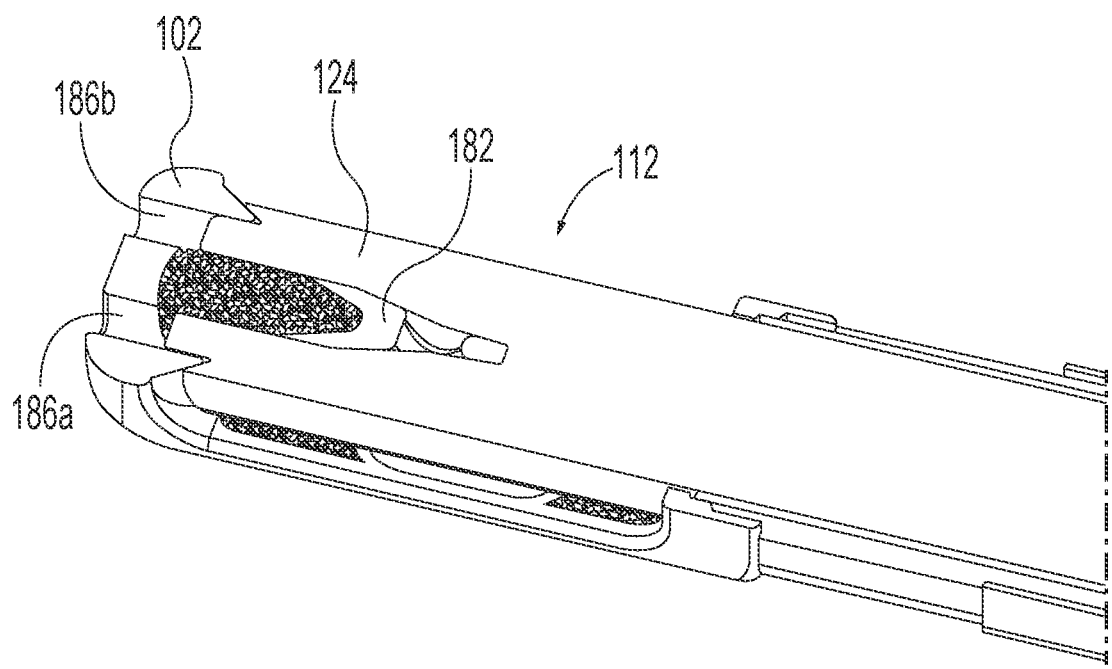
FIG. 9 is a cross-sectional, perspective view of the distal end of the impactor of FIG. 8 engaging a fusion cage.

Referring to FIG. 9, a cross-sectional view of the distal end 124 of the impactor 112 engaged with the fusion cage 102 is provided. As discussed in further detail below, the fusion cage 102 can have a ramp 182 and two forward apertures 186a, 186b in the ramp 182 to promote the dispersal of bone graft material in the disc space. The distal end 124 of the impactor 112 has a central slot that corresponds to the ramp 182 and two protrusions that correspond to the forward apertures 186a, 186b. As a result, the distal end 124 is secured to the fusion cage 102 in a lateral direction so the fusion cage 102 can be maneuvered into the disc space with a lateral movement. In addition, the impactor 112 transmits force from the head directly to the fusion cage 102 to drive the fusion cage 102 into the disc space in a longitudinal direction. As a result, the remaining components of the assembly do not need to be reinforced to withstand a striking device and the related forces.

Figure 10A:
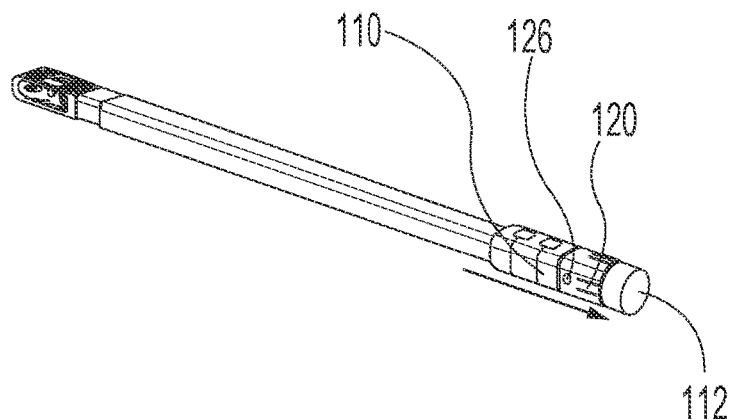
FIG. 10A is a perspective view of an impactor in a delivery assembly.
Figure 10B:
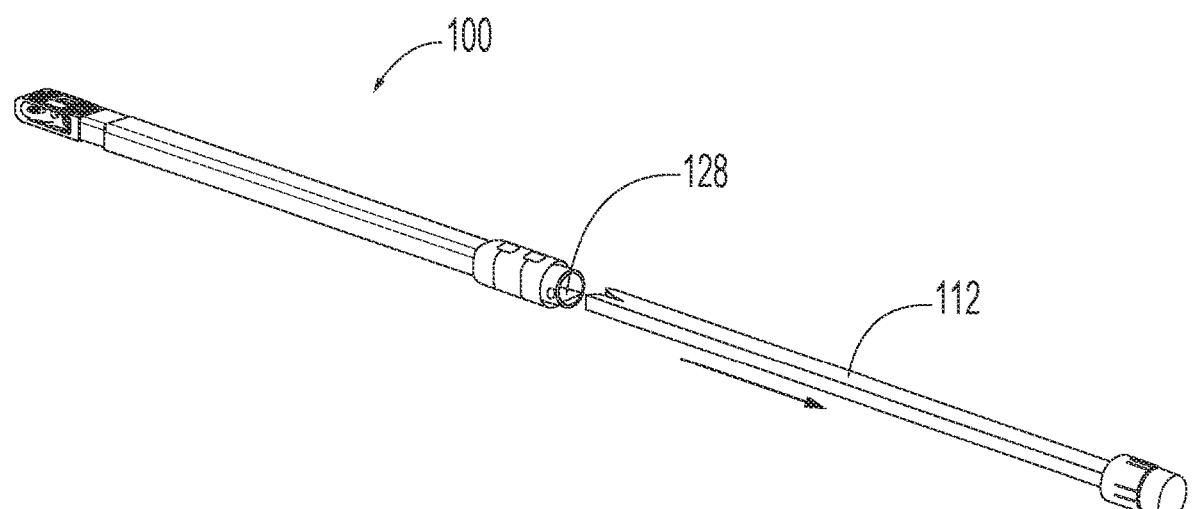
FIG. 10B is a perspective view of an impactor being removed from a delivery assembly.

Referring to FIGS. 10A and 10B, perspective views of the delivery assembly 100 and the impactor 112 are provided where the impactor 112 is removed from the delivery assembly 100. FIG. 10A shows the stud 126 of the lock collar 110 extending into the recess of the sleeve 120 of the impactor 112 to secure the impactor 112 to the assembly. To release the impactor 112 from the assembly, the impactor 112 rotates about a longitudinal axis, which is counterclockwise in this embodiment. Then, the impactor 112 is removed from the delivery assembly 100 as shown in FIG. 10B. Also shown in FIG. 10B is the channel 128 of the lock tube that extends through the lock tube to the fusion cage. This channel 128 can have a smooth bore to prevent components of the system or assembly from snagging or jamming.

Figure 11A:
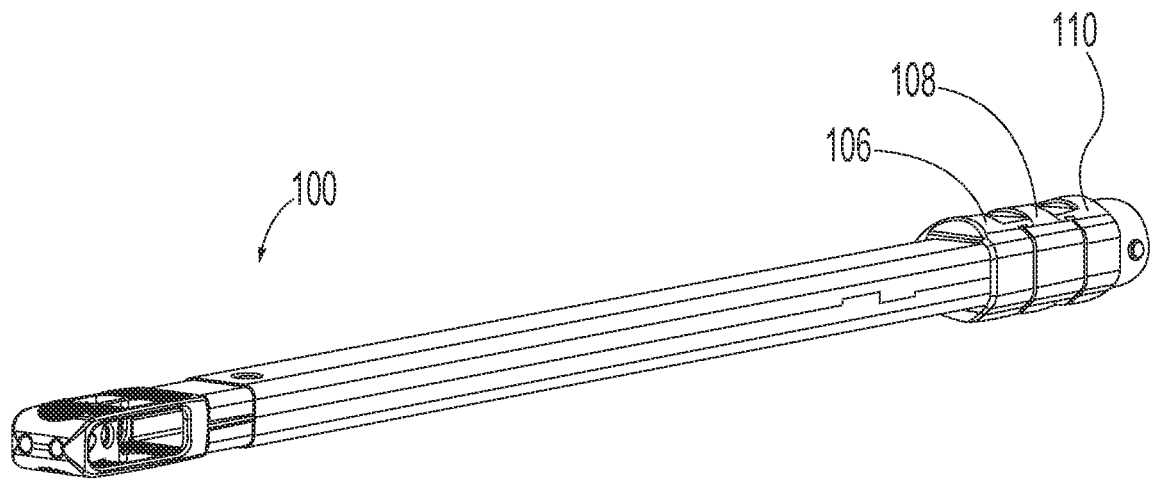
FIG. 11A is a perspective view of a delivery assembly with the impactor removed.
Figure 11B:
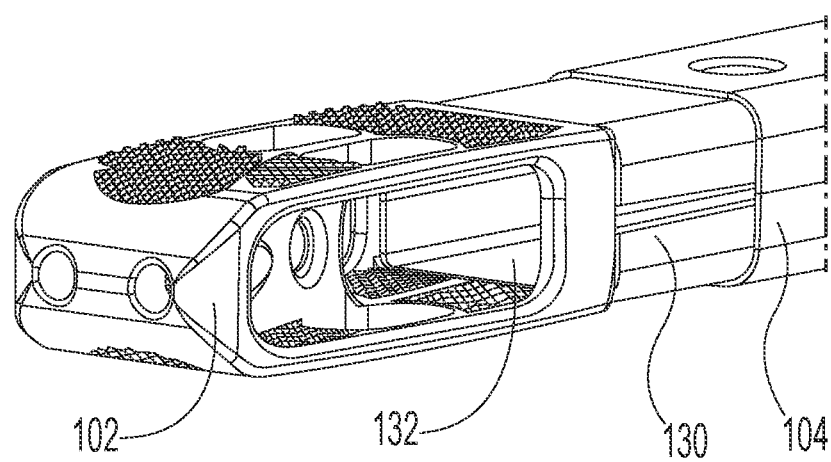
FIG. 11B is a detailed view of the delivery assembly of FIG. 11A.
Figure 38:
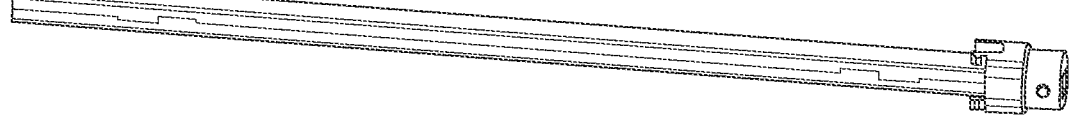
FIG. 38 is a perspective view of a lock tube.

Referring to FIGS. 11A and 11B, further perspective views of the delivery assembly 100 are provided. In these figures, the release collar 106, the inserter collar 108, and the lock collar 110 are shown as well as the respective release tube 104, inserter tube 130, and lock tube 132 (also see FIGS. 38-39). In these views, the fusion cage 102 is secured to the delivery assembly 100, specifically, the inserter tube 130. As discussed in further detail below, protrusions on deflectable arms of the inserter tube 130 are interlocked with protrusions or positioned in recesses of the fusion cage 102. The lock tube 132 prevents the arms of the inserter tube 130 from deflecting inward and releasing the fusion cage 102. After the lock tube 132 is removed, the release tube 104 can move toward a distal end of the inserter tube 130 to collapse the arms and take the protrusions out of engagement with the fusion cage 102 and release the fusion cage 102. This arrangement of tubes 104, 130, 132 allows for the secure attachment of the fusion cage 102 during initial positioning, bone graft delivery, and cover plate installation and then release at the conclusion of the procedure.

Figure 12A:
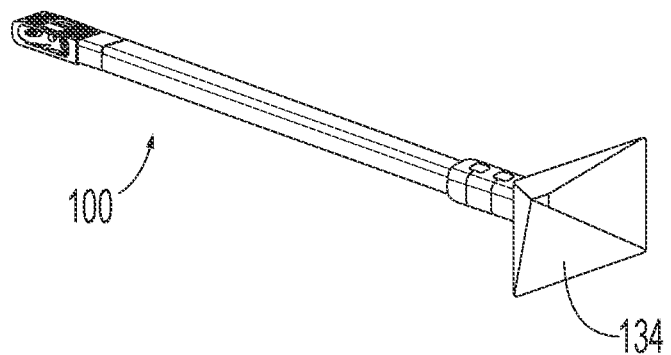
FIG. 12A is a perspective view of a funnel positioned on a proximal end of a delivery assembly.
Figure 12B:
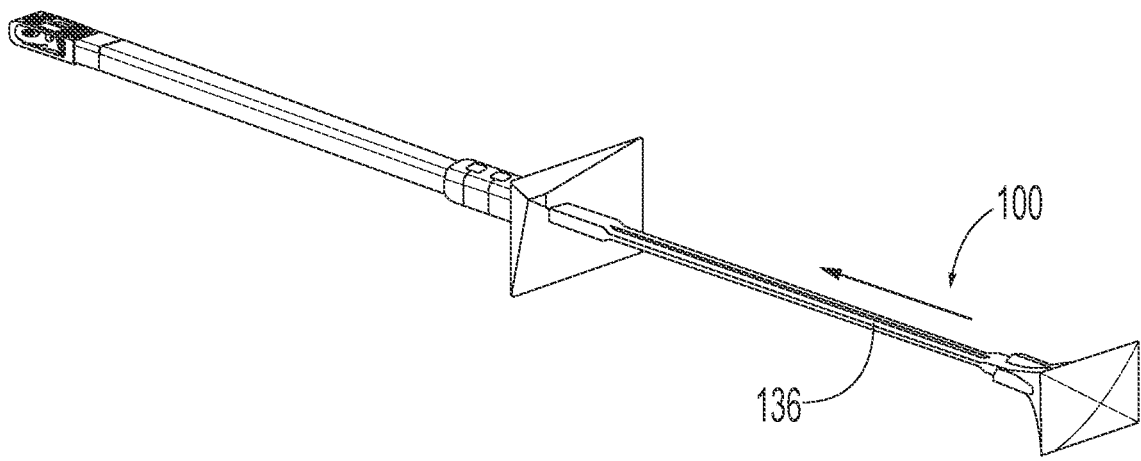
FIG. 12B is a perspective view of a plunger being inserted into a funnel and delivery assembly.
Figure 12C:
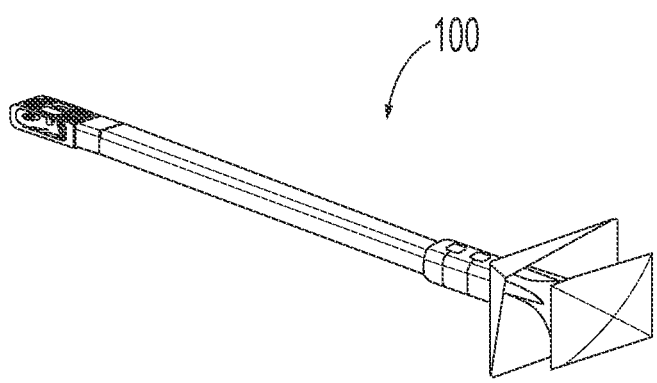
FIG. 12C is a perspective view of a plunger positioned in a funnel and delivery assembly.
Figure 37:
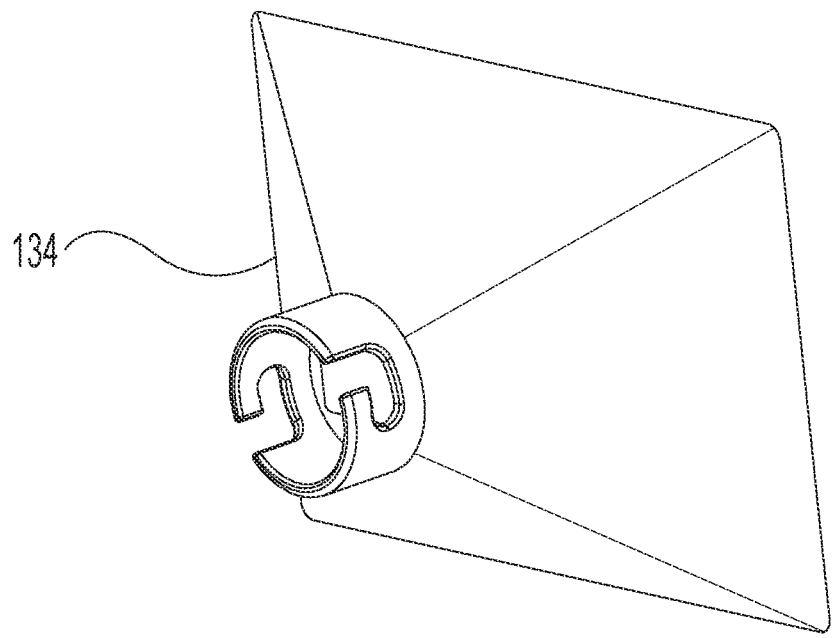
FIG. 37 is a perspective view of the distal side of a funnel.

Referring to FIGS. 12A-12C, perspective views of the delivery assembly 100 and a funnel 134 and plunger 136 are provided. The funnel 134 is positioned at the proximal end of the assembly 100 after the fusion cage has been positioned and after the impactor has been removed. The funnel 134 (i.e., its distal side) is also illustrated in FIG. 37. As described elsewhere herein, bone grafting material can be loaded into the funnel 134 and assembly 100. Then, the plunger 136 drives the bone graft material through the channel of the lock tube, through the fusion cage, and into the disc space. As described in further detail below, the fusion cage has an arrangement of features that direct the bone graft material in desired directions and desired proportions and help promote the osseointegration of bone, bone graft material, and the fusion cage. It will be appreciated that embodiments of the present disclosure encompass other loading techniques and devices besides a funnel 134 and plunger 136. For instance, the delivery assembly can include a breech type loader in a proximal end of the lock tube. See, e.g., U.S. Prov. App. No. 62/900,960, to which the present application claims priority, and which is incorporated herein by reference in its entirety.

Figure 13:
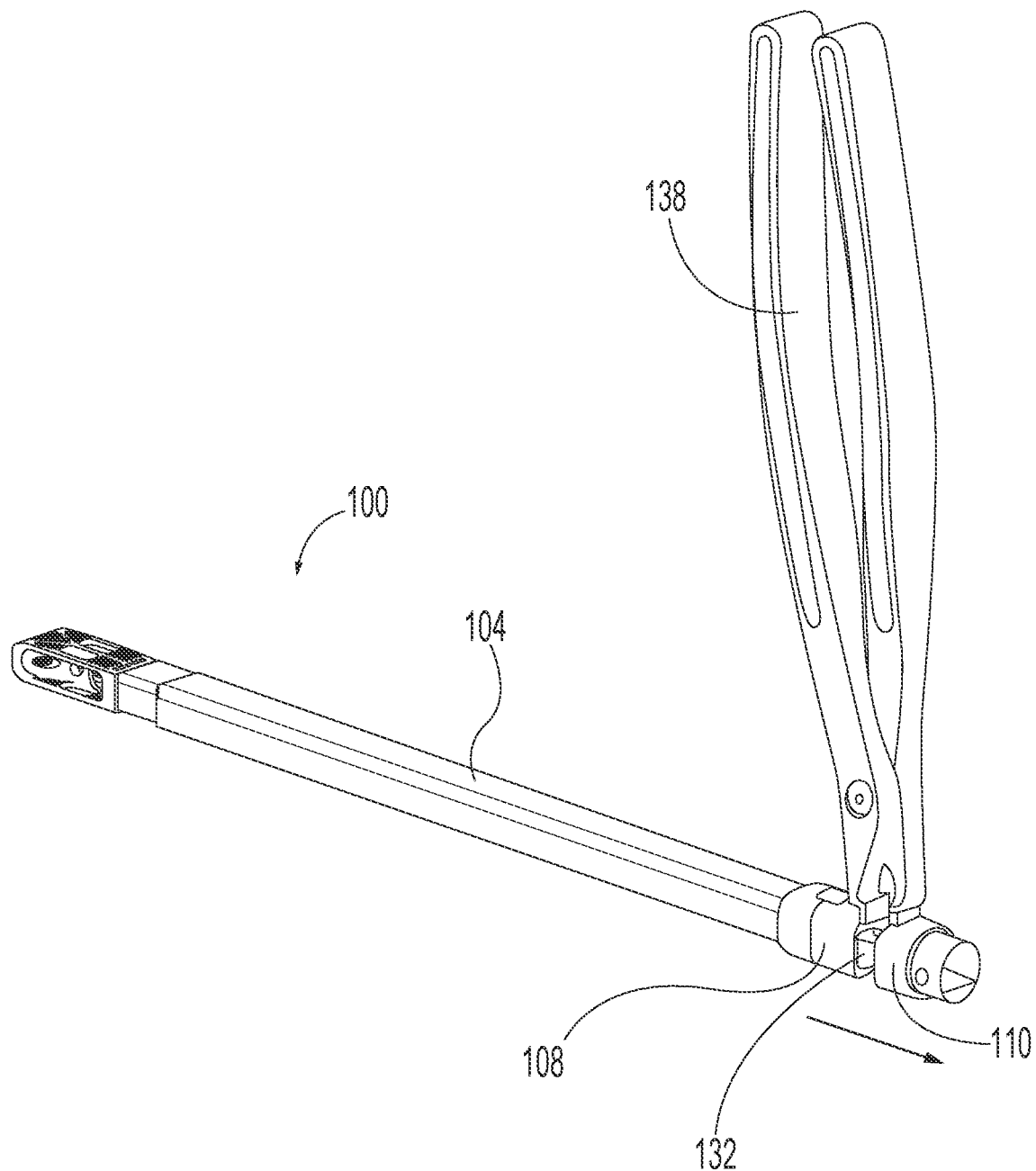
FIG. 13 is a perspective view of pliers removing a lock tube from a delivery assembly.

Referring to FIG. 13, a perspective view of a delivery assembly 100 is provided where the lock tube 132 is being removed from the assembly 100. Pliers 138 are positioned between the lock collar 110 and the inserter collar 108, and the pliers 138 drive the collars 108, 110 apart. As a result, the lock tube 132 is driven relative to the other tubes of the assembly 100 along a longitudinal axis, and the lock tube 132 is removed from the delivery assembly 100.

Figure 14A:
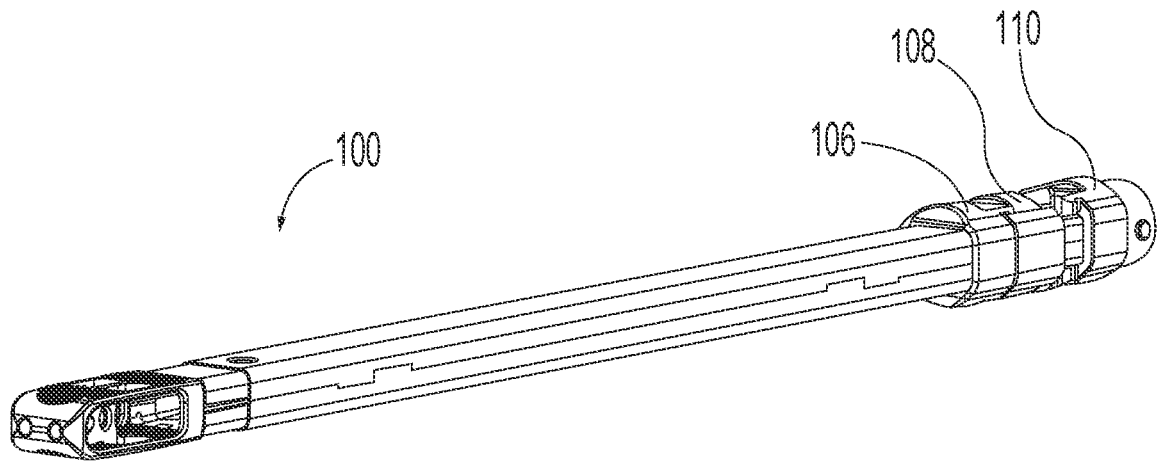
FIG. 14A is a perspective view of a delivery assembly with a lock tube partially removed.
Figure 14B:
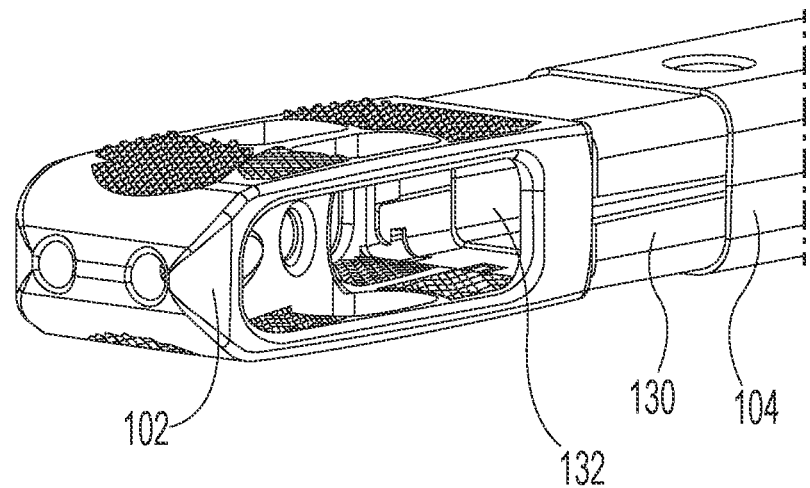
FIG. 14B is a detailed view of the delivery assembly of FIG. 14A.

Referring to FIGS. 14A and 14B, further perspective views of a delivery assembly 100 are provided where the lock tube 132 is being removed from the assembly 100. FIG. 14A shows the lock collar 110 separated from the inserter collar 108 by a distance. Similarly, FIG. 14B shows a distal end of the lock tube 132 separated from a distal end of the inserter tube 130 by the same distance. Prior to the lock tube 132 being removed, the distal ends of the lock tube 132 and the inserter tube 130 are located at substantially the same position along a longitudinal axis of the assembly 100 to keep the protrusions of the arms of the inserter tube 130 positively engaged with the fusion cage 102.

Figure 15A:
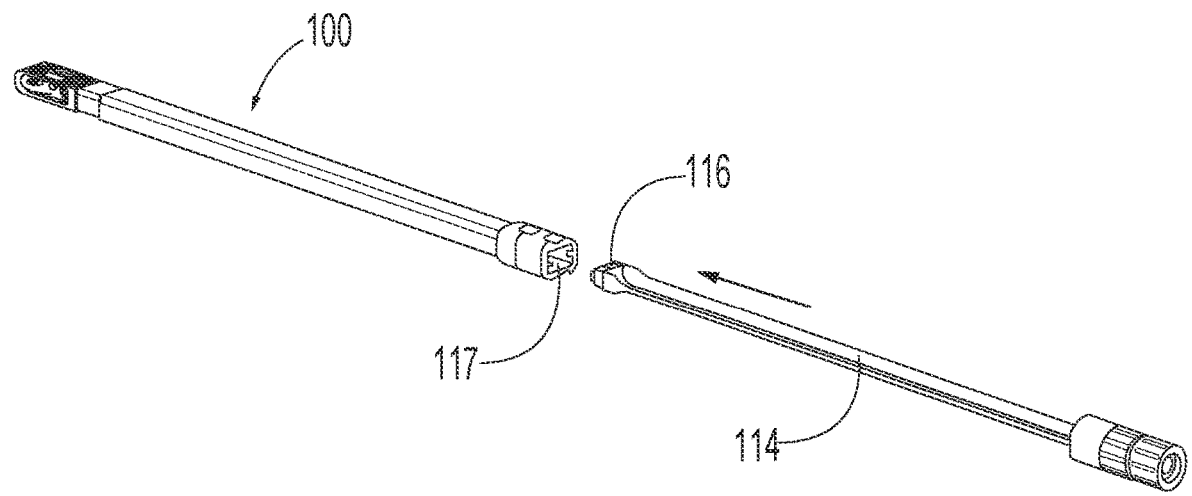
FIG. 15A is a perspective view of an inserter being positioned in a delivery assembly.
Figure 15B:
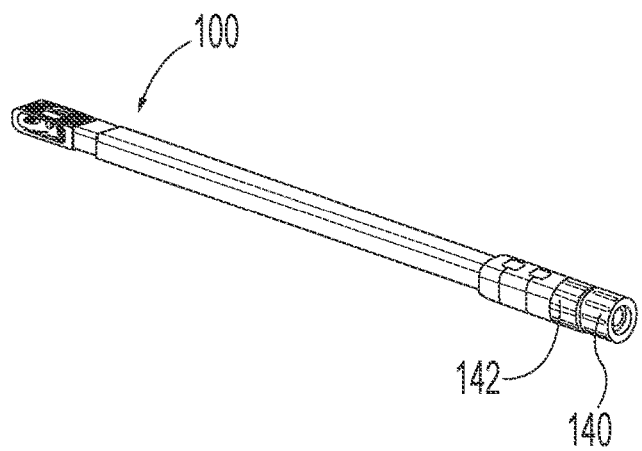
FIG. 15B is a perspective view of an inserter positioned in a delivery assembly.
Figure 15C:
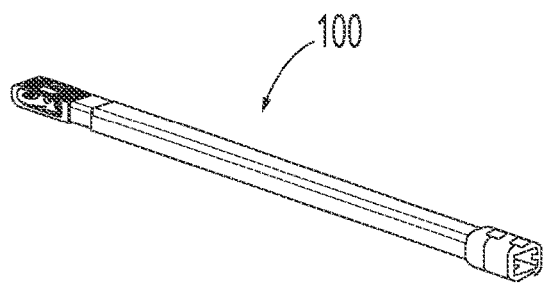
FIG. 15C is a perspective view of a delivery assembly after removal of an inserter.

Referring to FIGS. 15A-15C, perspective views of the delivery assembly 100 and inserter 114 are provided. The inserter 114 positions and secures a cover plate 116 in the fusion cage to keep bone graft material secured in the disc space. First, the cover plate 116 is selectively engaged to a distal end of the inserter 114. Then, the cover plate 116 and inserter 114 extend through a channel 117 in the inserter tube. Once the inserter 114 is fully positioned in the assembly 100 and the cover plate 116 has reached the fusion cage, a first sleeve 140 of the inserter 114 can be manipulated to secure the cover plate 116 to the fusion cage. As discussed in further detail below, the first sleeve 140 is connected to a rod that extends through the inserter 114 to the cover plate 116. The rod can extend in the longitudinal direction to position a wedge of the cover plate 116 and then rotate the wedge to lock tabs of the cover plate 116 into the fusion cage to secure the cover plate 116 to the fusion cage. Then, a second sleeve 142, which is connected to a sheath disposed about the rod, can be manipulated to rotate a threaded end of the sheath out of the cover plate to release the inserter 114 from the cover plate 116. Finally, the inserter 114 can be removed from the assembly 100.

Figure 16A:
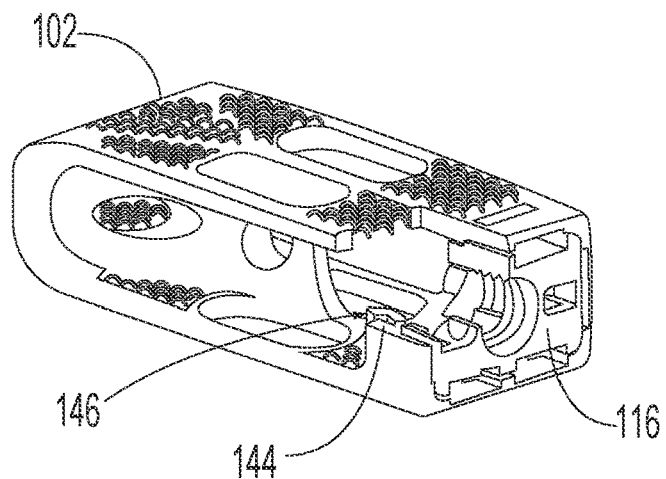
FIG. 16A is a perspective view of a cover plate positioned in a fusion cage with a tab of the cover plate in an inward, unsecured position.
Figure 16B:
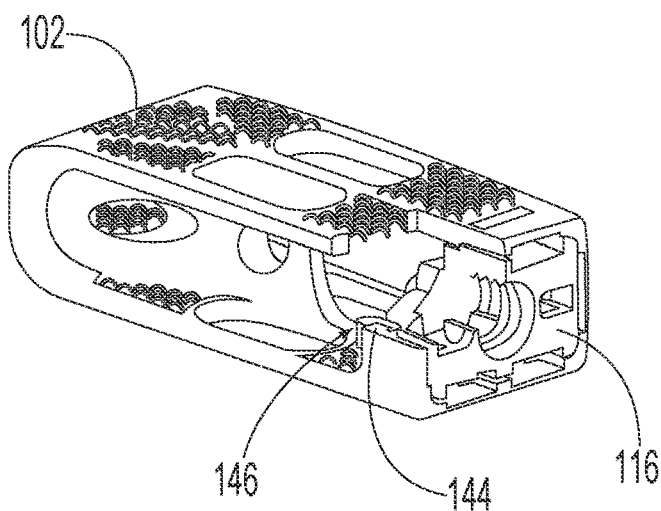
FIG. 16B is a perspective view of a cover plate positioned in a fusion cage with a tab of the cover plate in an outward, secured position.
Figure 16C:
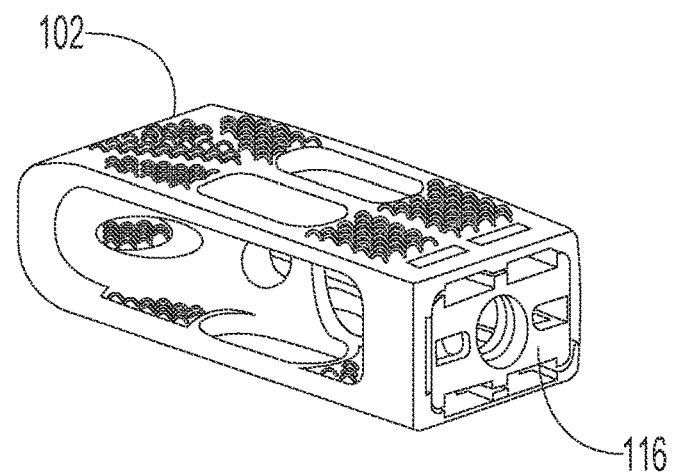
FIG. 16C is a perspective view of a cover plate secured within a fusion cage.
Figure 27:
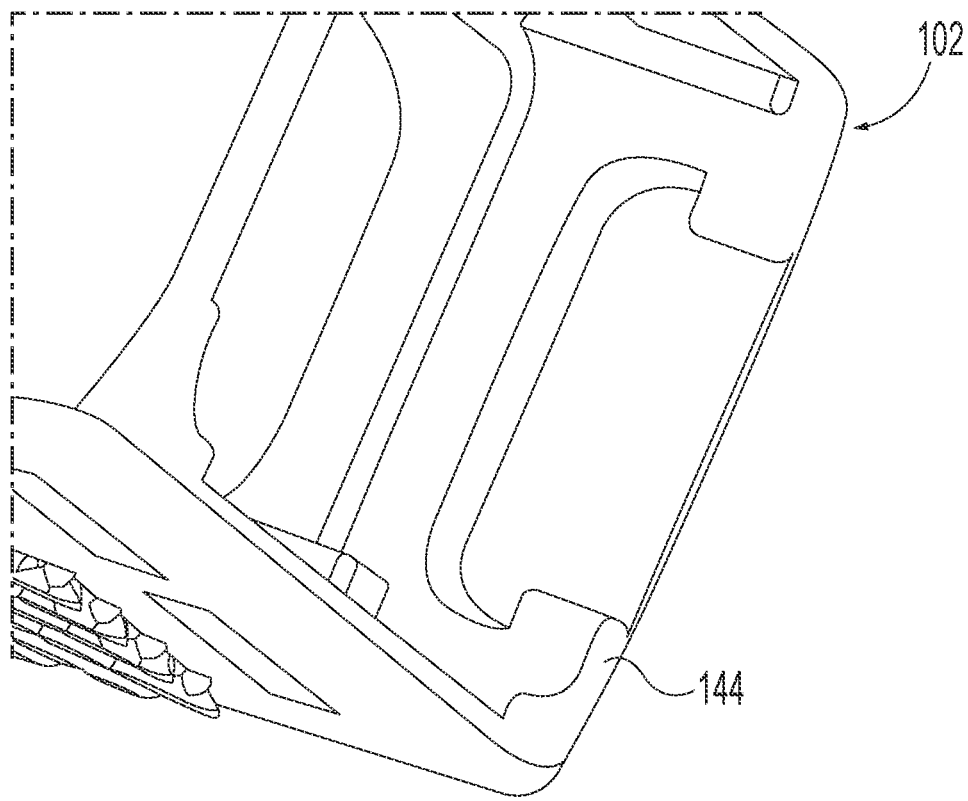
FIG. 27 is a perspective view of the proximal end of the side of a fusion cage.
Figure 28:
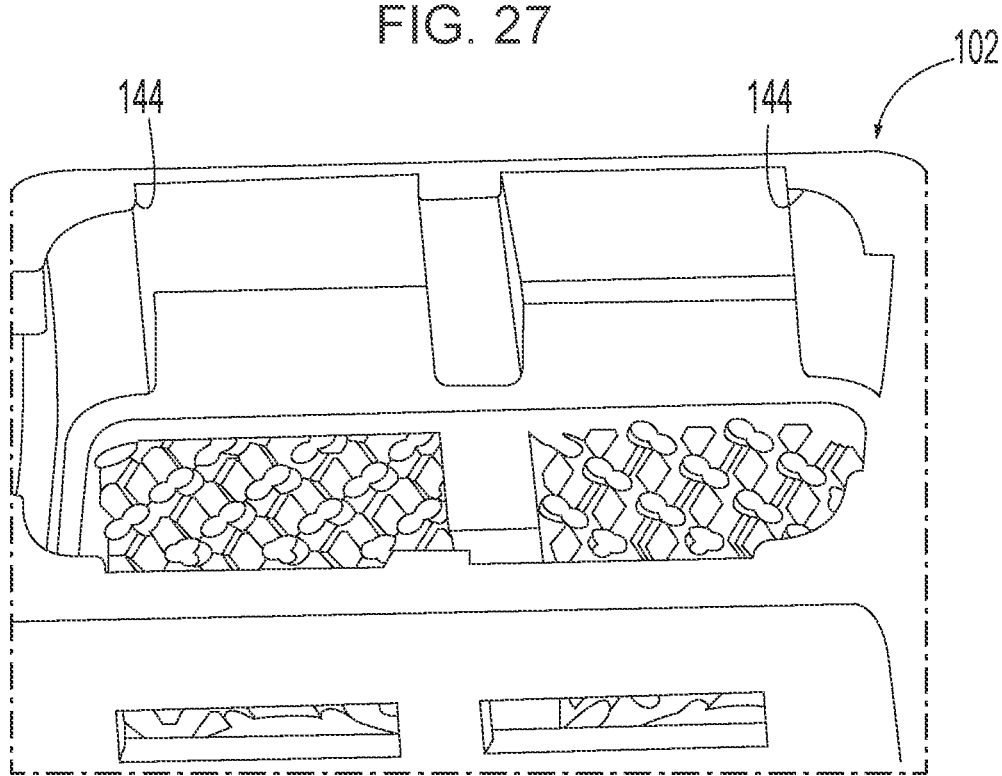
FIG. 28 is a perspective view of the proximal portion of the top of a fusion cage.

FIGS. 16A-19B show the relationship between the various features of the inserter 114, the cover plate 116, and the fusion cage 102 that allow the cover plate to be secured to the fusion cage and retain the bone graft material within the disc space. FIGS. 16A-16C include partial cross-sectional views that show the cover plate 116 and the fusion cage 102 being secured together. The fusion cage 102 has an inwardly extending protrusion 144 (also see FIGS. 27-28), and the cover plate 116 has an outwardly extending tab 146 (also see FIGS. 31-33). The tab 146 is positioned on a distal side of the protrusion 144, and the tab 146 is deflectable, or moveable, between an inward, unsecured position and an outward, secured position where the tab 146 and protrusion 144 interlock. FIG. 16A shows the tab 146 in an inward, unsecured position, FIG. 16B shows the tab 146 in an outward, secured position, and FIG. 16C is a perspective view of the cover plate 116 and the fusion cage 102. It will be appreciated that the present disclosure encompasses different numbers and configurations of protrusions 144 and tabs 146.

Figure 17A:
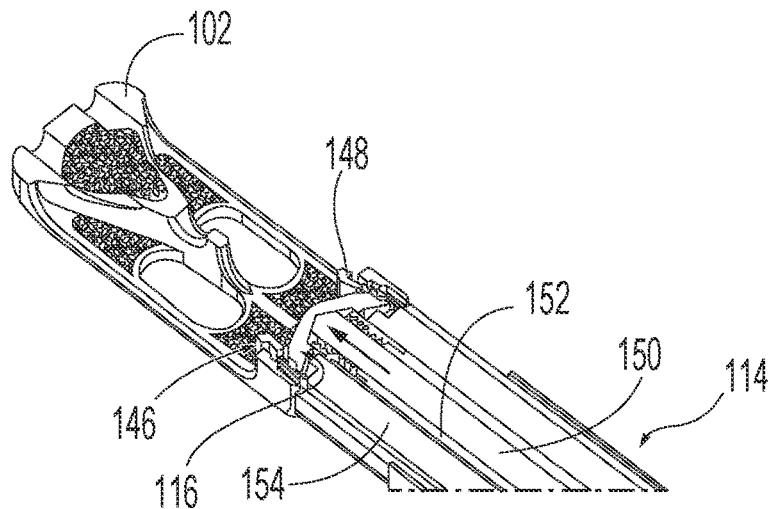
FIG. 17A is a cross-sectional view of an inserter, a cover plate, and a fusion cage.
Figure 17B:
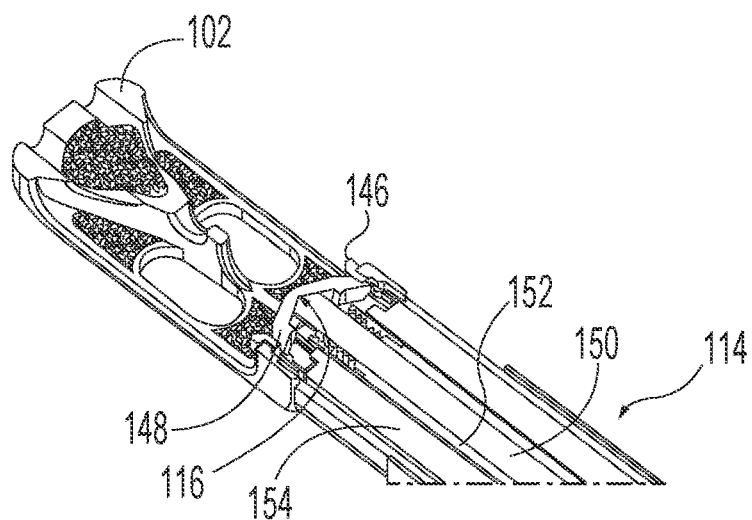
FIG. 17B is a cross-sectional view of a rod of an inserter pushing a wedge of a cover plate.
Figure 17C:
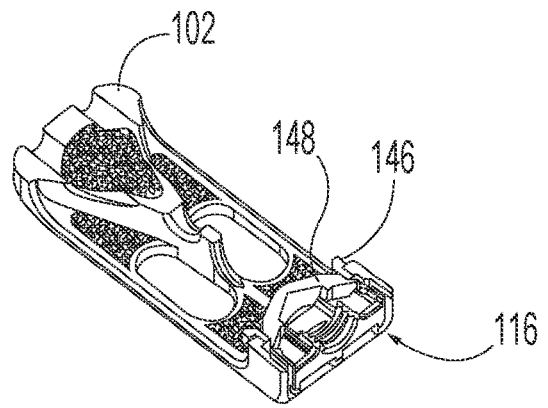
FIG. 17C is a cross-sectional view of a rod rotating a wedge to secure a cover plate to a fusion cage.
Figure 34:
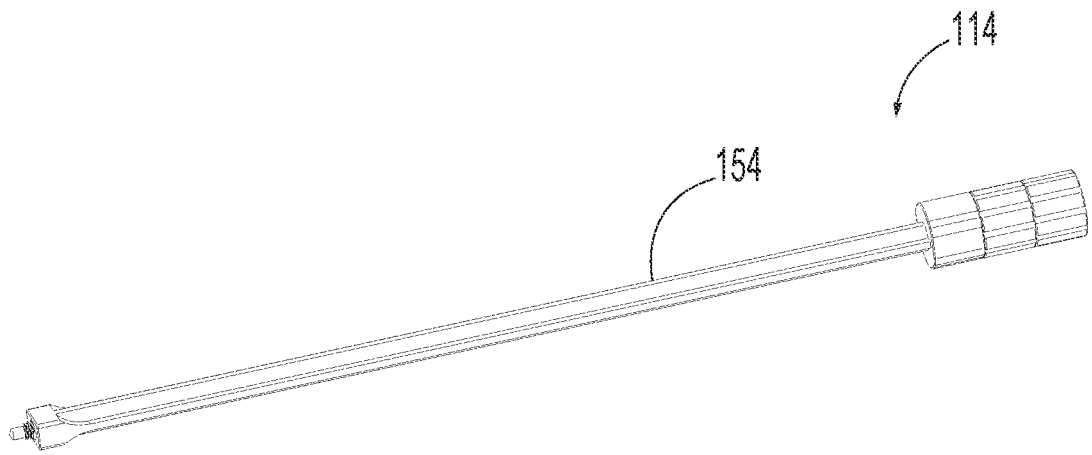
FIG. 34 is a perspective view of an inserter tube.
Figure 35:
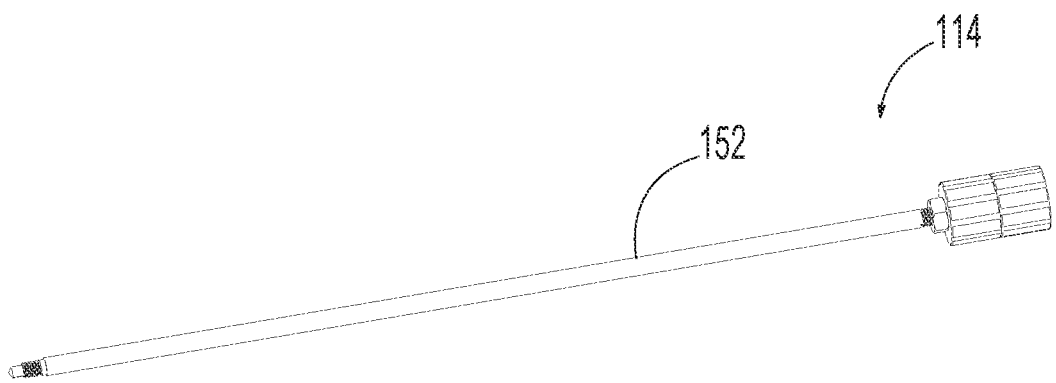
FIG. 35 is a perspective view of an inserter tube with its second outer sheath removed.
Figure 36:
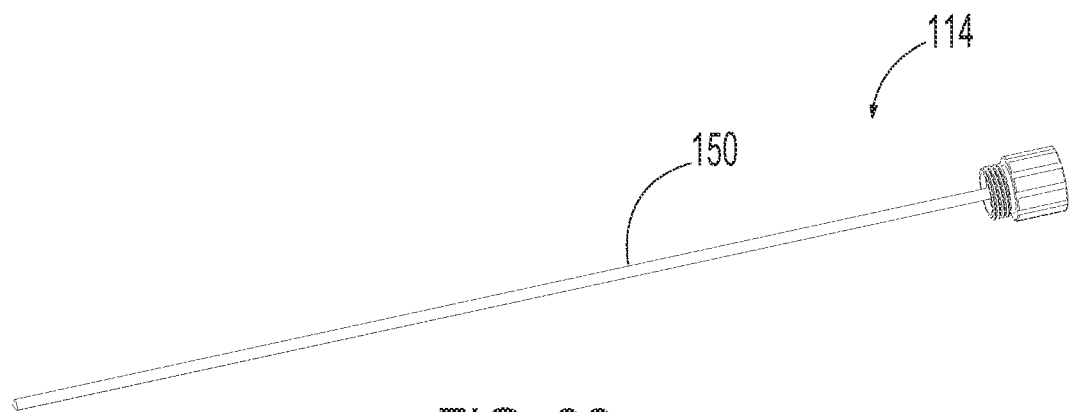
FIG. 36 is a perspective view of an inserter tube with its first and second sheaths and second sleeve removed, exposing its rod and first sleeve.

Referring to FIGS. 17A-17C, cross-sectional, perspective views of the inserter 114 and the fusion cage 102 are provided. The inserter 114 has a central rod 150, a first sheath 152 positioned about the rod 150, and a second sheath 154 positioned about the first sheath 152 (also see FIGS. 34-36). The tab 146 of the cover plate 116 is shown as well as a wedge 148 of the cover plate 116. The rod 150 operably engages the wedge 148 to push the wedge 148 into alignment with the tab 146 in the longitudinal direction. Then, as shown in FIG. 17B, the rod 150 rotates the wedge 148 about the longitudinal axis to deflect the tab 146 outward and secure the cover plate 116 to the fusion cage 102. Then, the first sheath 152 can unthread from a threaded aperture of the cover plate 116, and the inserter 114 can be removed from the delivery assembly as shown in FIG. 17C.

Figure 18A:
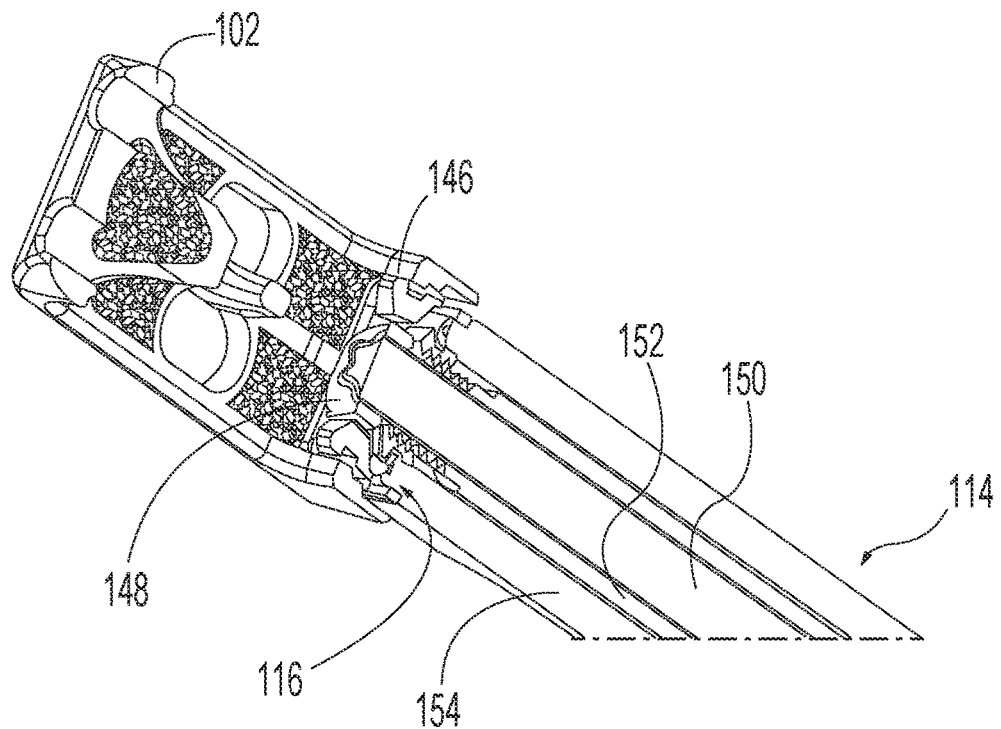
FIG. 18A is a cross-sectional view of a fusion cage and a wedge of a cover plate in a first position.
Figure 18B:
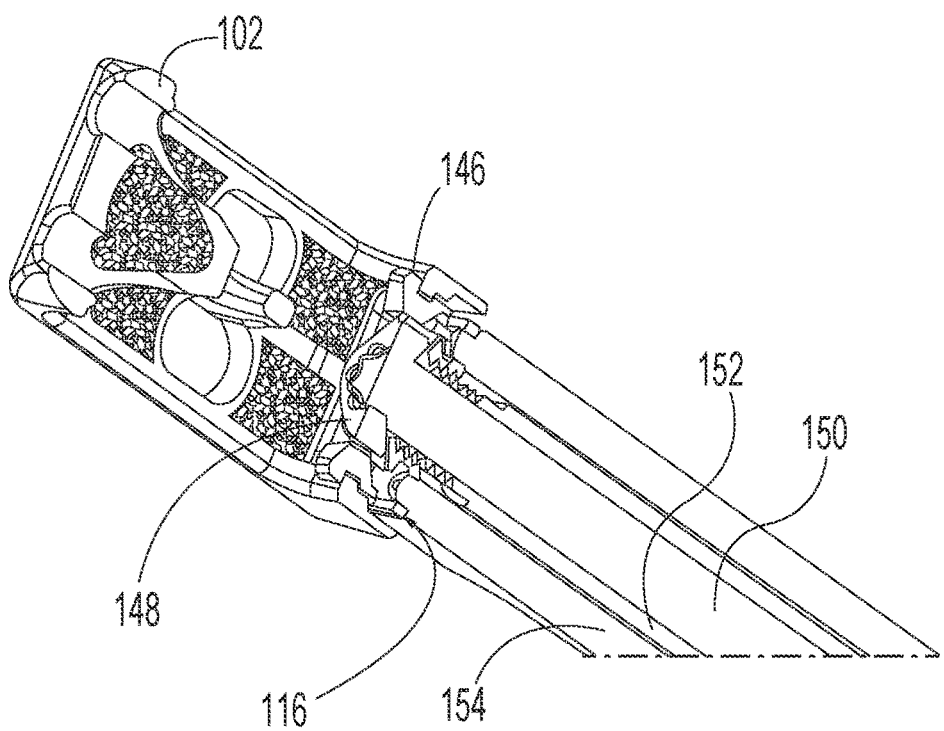
FIG. 18B is a cross-sectional view of a fusion cage and a wedge of a cover plate in a second position.

Referring to FIGS. 18A and 18B, additional cross-sectional, perspective views of the inserter 114, the cover plate 116, and the fusion cage 102 are provided. From this perspective, the shape of the distal end of the rod 150 and the inner aperture of the wedge 148 are shaped such that rotation of the rod 150 rotates the wedge 148. In this embodiment, the shape is a hexagonal pattern, but it will be appreciated that embodiments of the present disclosure encompass any shape that translates rotational motion and force from one component to another component.

Figure 19A:
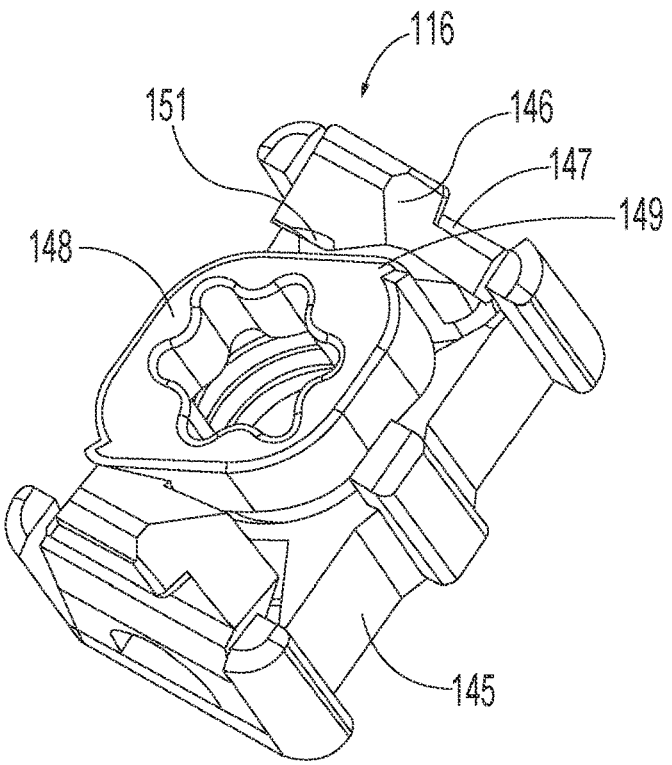
FIG. 19A is a cross-sectional view of a wedge of a cover plate in a first position.
Figure 19B:
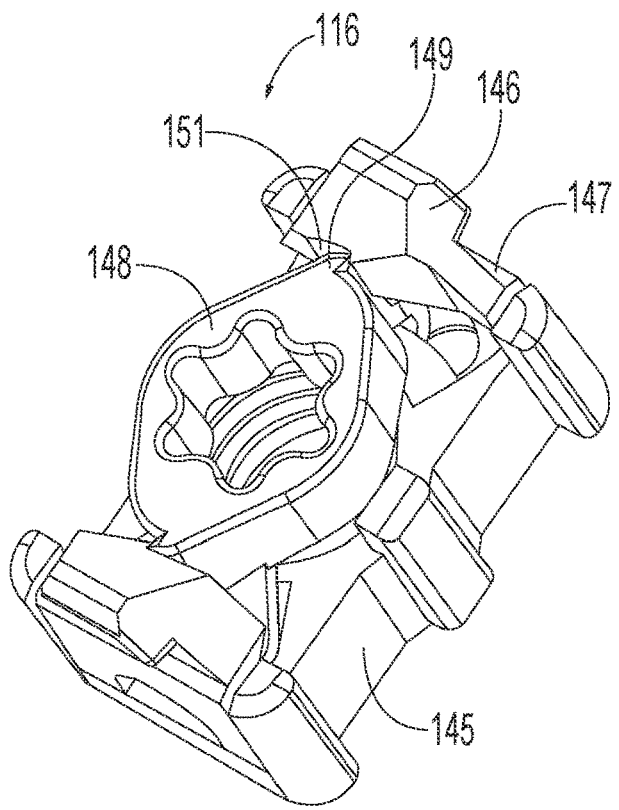
FIG. 19B is a cross-sectional view of a wedge of a cover plate in a second position.
Figure 31:
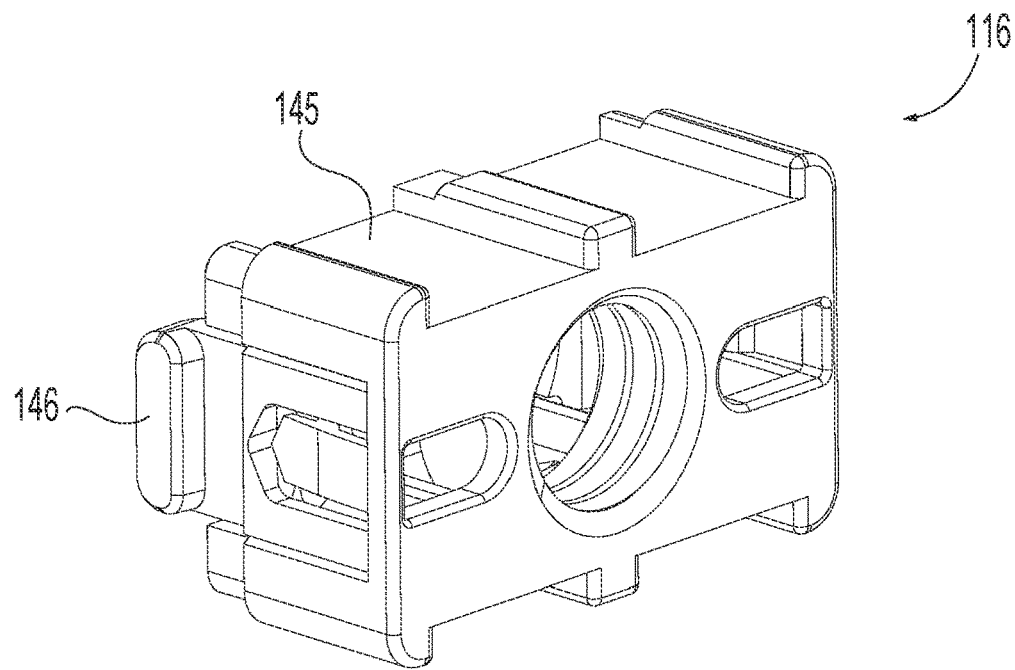
FIG. 31 is a perspective view of the proximal side of a cover plate.
Figure 32:
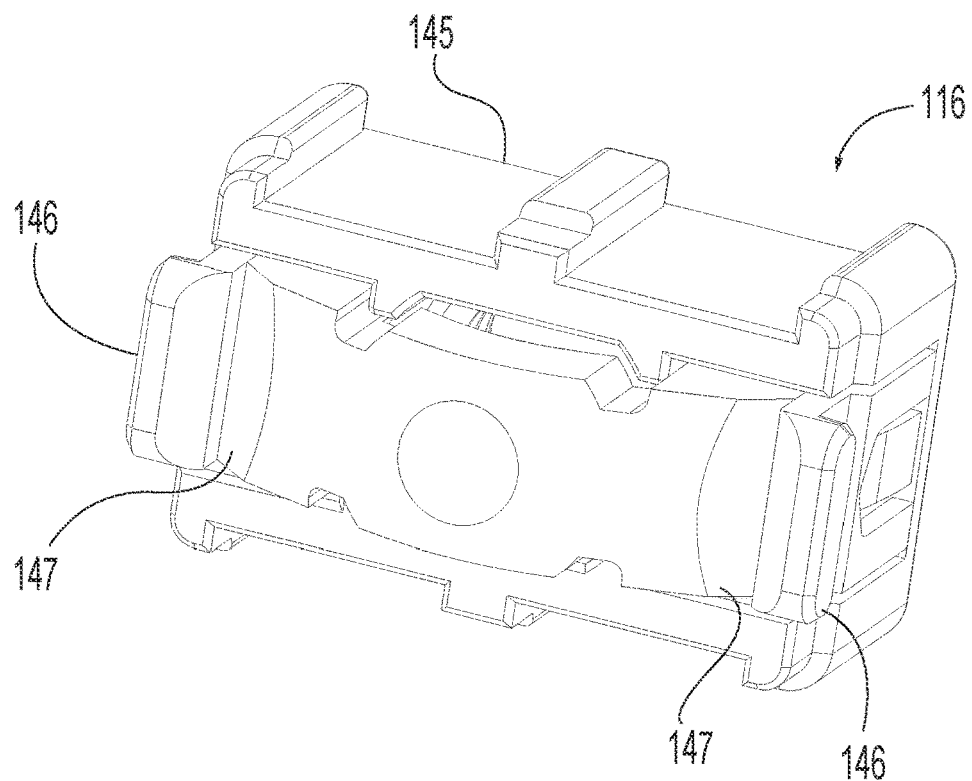
FIG. 32 is a perspective view of the distal side of a cover plate.
Figure 33:
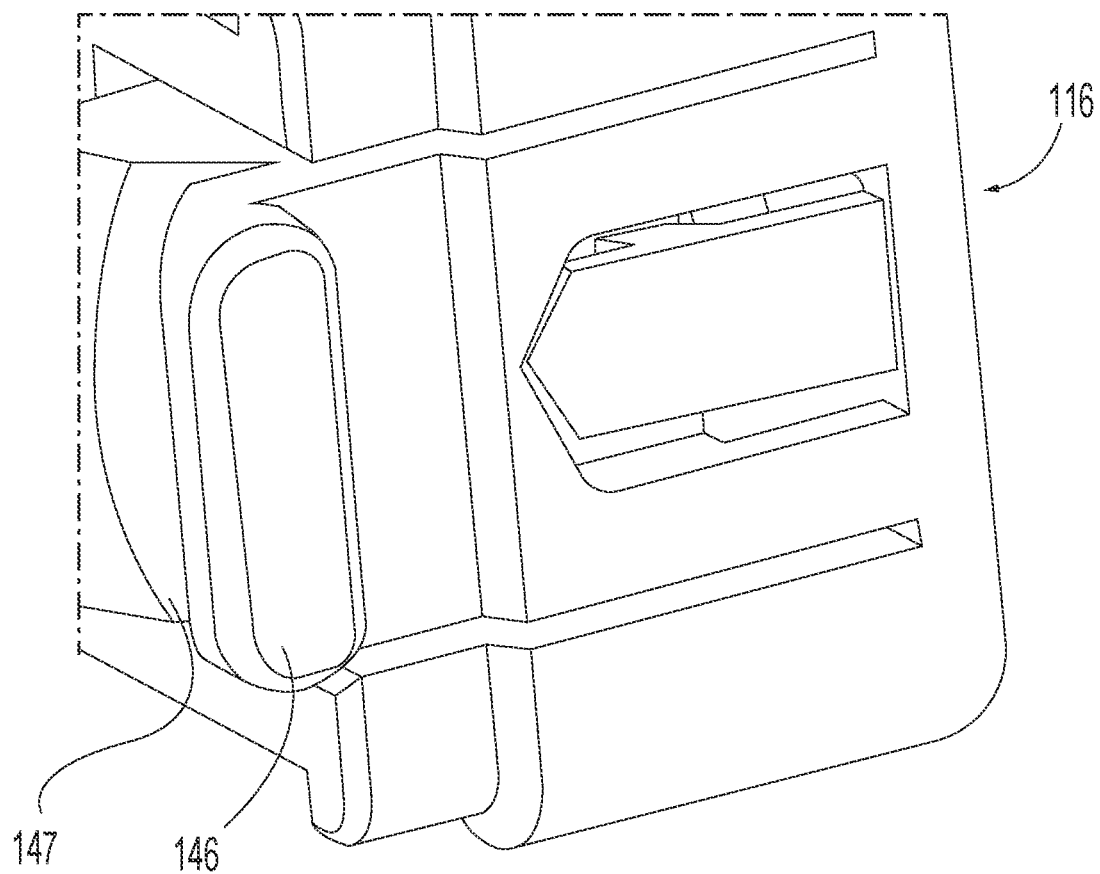
FIG. 33 is a perspective view of the tab of a cover plate.

Referring to FIGS. 19A and 19B, perspective views of the cover plate 116 in an unsecured state and a secured state are provided, respectively. The cover plate 116 generally comprises a body 145, a wedge 148, and two tabs 146. A portion of the tab 146 extends outwardly at a distal end of the tab 146 to define a recess 147 in which the protrusion of the fusion cage can extend into to secure the cover plate 116 and the fusion cage together. In FIG. 19A, the tab 146 is in an undeflected position, and the wedge 148 is in a first position. In 19B, the rod has rotated the wedge 148 to a second position, and a protrusion 149 on an outer surface of the wedge 148 has driven into the tab 146 to deflect the tab 146 to an outward position. In addition, the protrusion 149 resides in a recess 151 in the tab 146 to maintain the tab 146 in the outward position and the cover plate 116 secured to the fusion cage. Additional views of the cover plate 116 are shown in FIGS. 31-33, wherein the wedge 148, protrusion 149 and recess 151 have been removed for the sake of illustration.

Figure 20A:
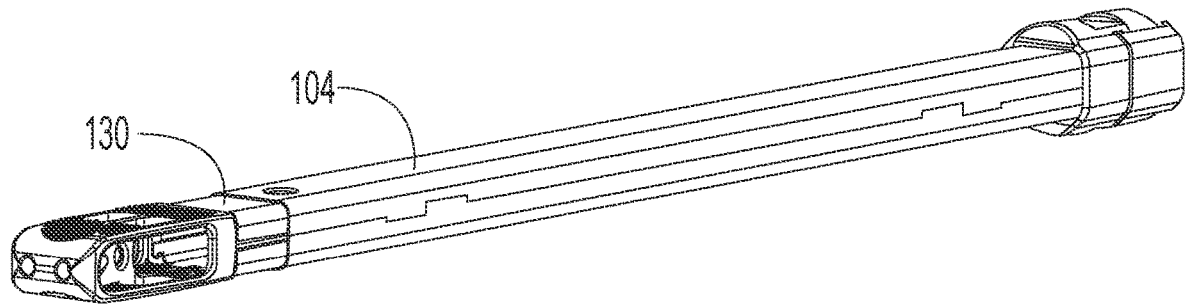
FIG. 20A is a perspective view of a delivery assembly with a release tube and an inserter tube.

FIGS. 20A-24 generally show the selective connection between the fusion cage 102 and the inserter tube 130, specifically the release of the fusion cage 102 from the inserter tube 130 after the cover plate has been secured to the fusion cage 102. Referring to FIGS. 20A and 20B, perspective views of the inserter tube 130 comprising a first arm 156 and a second arm 158 are provided. Each arm is deflectable between an inward position where the fusion cage 102 can be released from the inserter tube 130 and an outward position where the fusion cage 102 and the inserter tube 130 are secured together. It will be appreciated that in various embodiments, the arms 156, 158 are biased toward the outward position. In some embodiments, the arms 156, 158 are biased toward the inward position. In yet further embodiments, the arms 156, 158 are unbiased or biased to a point between the inward and outward positions. As discussed elsewhere herein, the lock tube and the inserter prevent the arms 156, 158 from deflecting inward and unintentionally releasing the fusion cage 102 from the inserter tube 130.

Figure 20B:
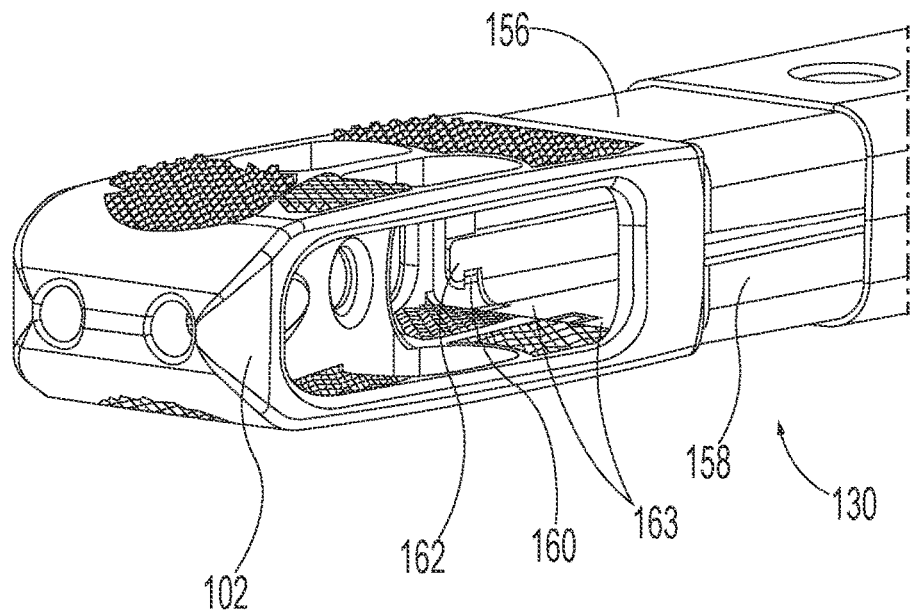
FIG. 20B is a detailed view of the delivery assembly of FIG. 20A.
Figure 29:
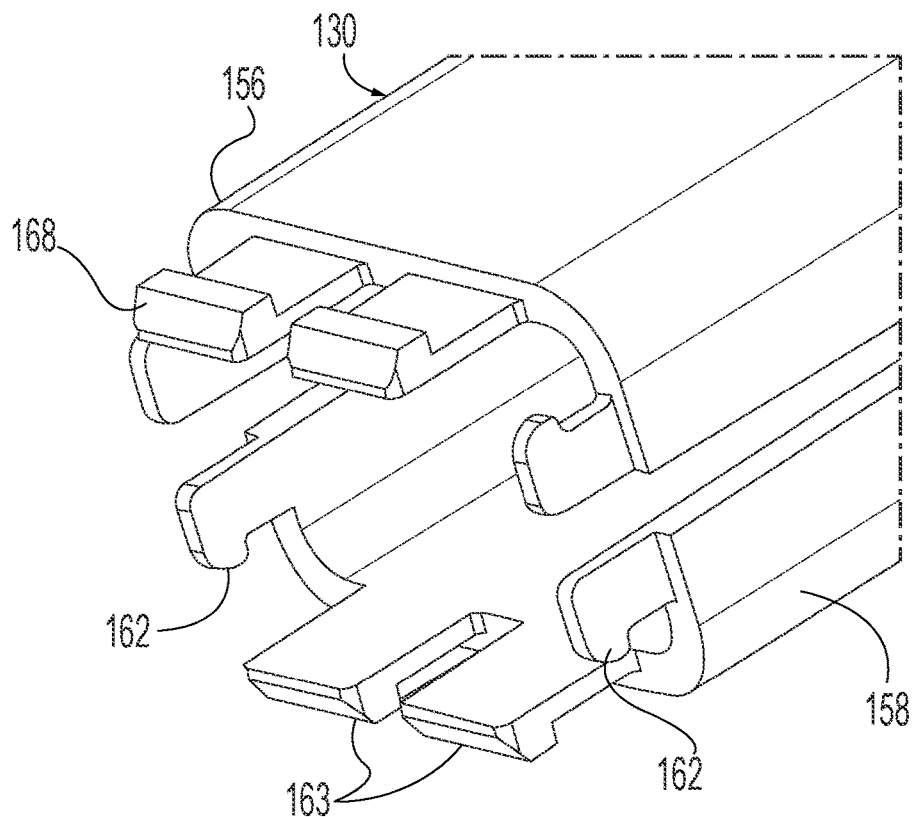
FIG. 29 is a perspective view of the distal end of an inserter tube.
Figure 30:
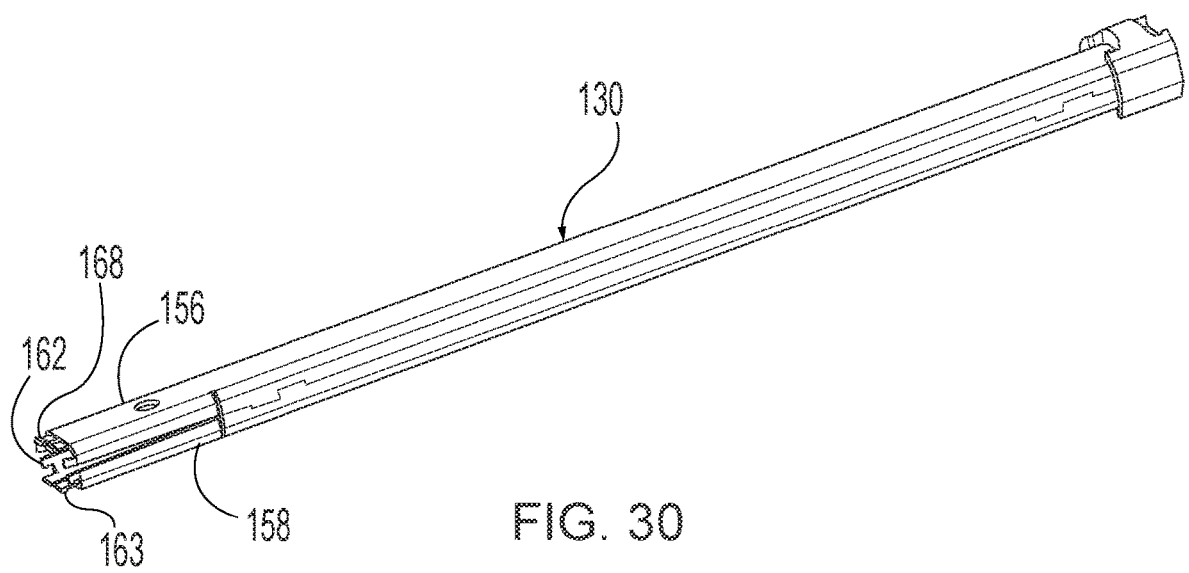
FIG. 30 is a perspective view of an inserter tube.

FIGS. 20A and 20B also show that a distal end of the second arm 158 has a protrusion 162 that extends downward toward a bottom side of the assembly. Another protrusion 160 extends from the fusion cage 102 upward toward a top side of the assembly. These protrusions 160, 162 interlock to secure the fusion cage 102 and the inserter tube 130 together. It will be appreciated that the second arm 158 can have a first side protrusion 162 and a second side protrusion (not shown) that extend downward to interlock with protrusions 160 of the fusion cage 102. Further, the second arm 158 can have two protrusions 163 on a bottom surface of the arm 158 that extend downwardly into recesses or apertures in the fusion cage 102. Similarly, the first arm 156 can have two side protrusions and two top protrusions that extend upwardly toward a top surface of the assembly. The foregoing features of the inserter tube 130 are also illustrated in FIGS. 29 and 30.

Figure 21A:
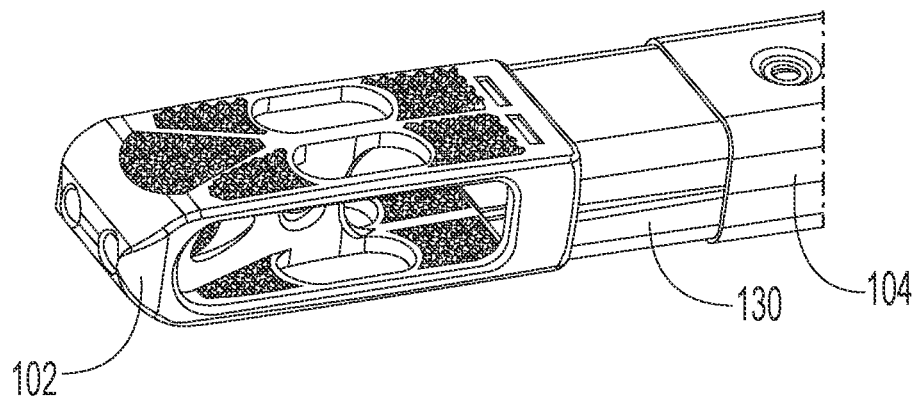
FIG. 21A is a perspective view of a release tube, an inserter tube, and a fusion cage.
Figure 21B:
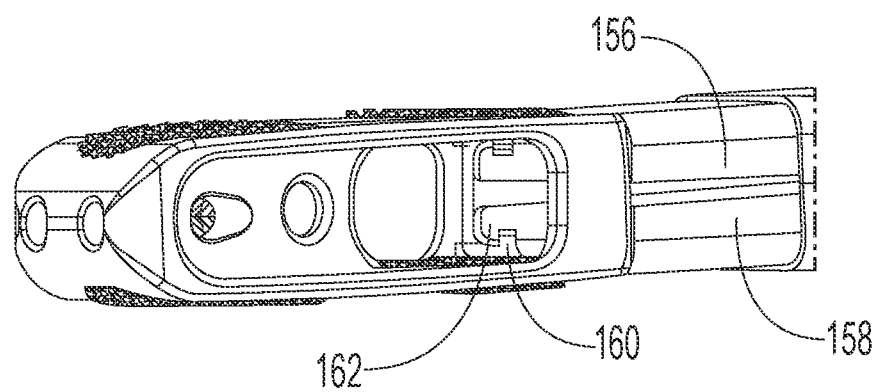
FIG. 21B is a further perspective view of the release tube, the inserter tube, and the fusion cage of FIG. 21A.
Figure 21C:
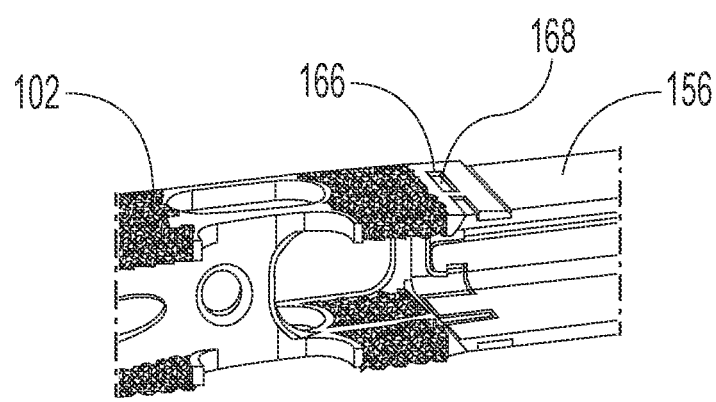
FIG. 21C is a partial cross-sectional view of the release tube, the inserter tube, and the fusion cage of FIG. 21A.

Referring to FIGS. 21A-21C, further perspective views of the fusion cage 102 and the inserter tube are provided. FIG. 21C shows a top protrusion 168 of the first arm 156 extending into a recess 166 of the fusion cage 102. While the arms of the inserter tube 130 each have four protrusions (see FIGS. 29 and 30), it will be appreciated that embodiments of the present disclosure can encompass various numbers and configurations of protrusions of the inserter tube 130 that interlock with other protrusions, depressions, recesses, etc. of the fusion cage 102.

Figure 22:
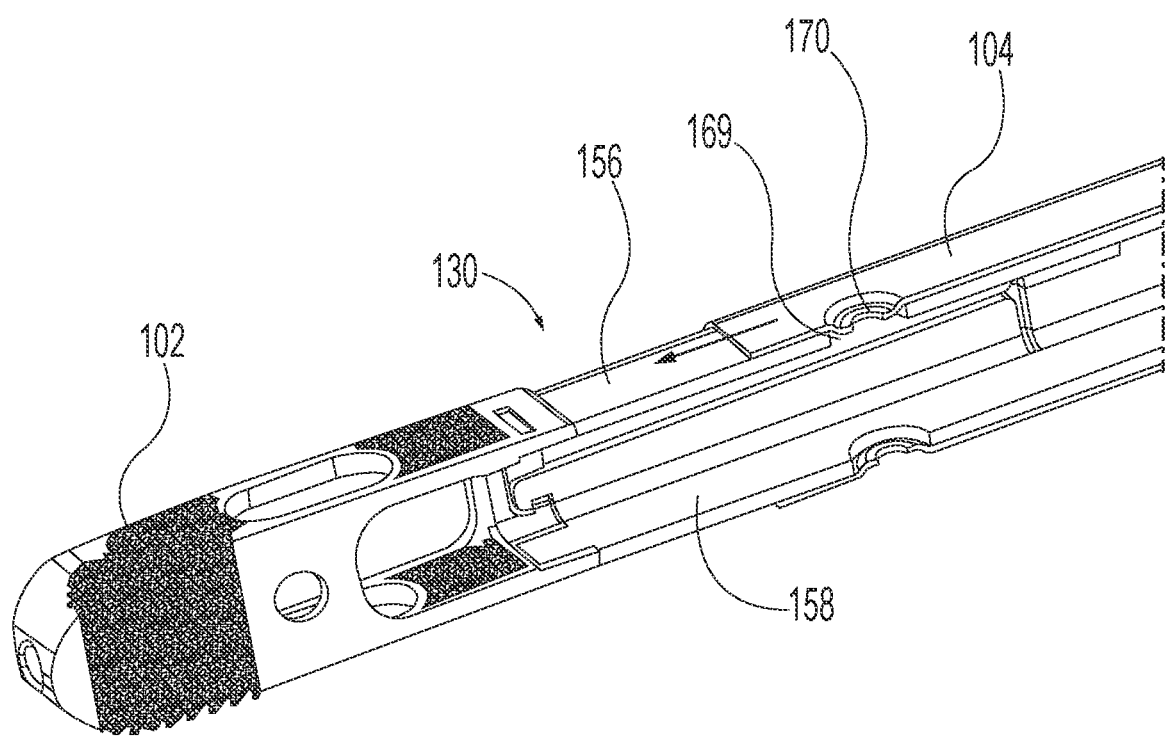
FIG. 22 is a perspective view of a release tube moving relative to an inserter tube and a fusion cage.

Referring to FIG. 22, a perspective view of a fusion cage 102, a release tube 104, and an inserter tube 130 is provided. Here, the release tube 104 is moving relative to the inserter tube 130 and the fusion cage 102 to release the fusion cage 102 from the inserter tube 130. During the previously-described actions, the distal end of the release tube 104 is offset from the distal end of the inserter tube 130, and a protrusion 170 of the first arm 156 extends inwardly into an aperture 169 of the first arm 156 to maintain the relative positions of the tubes 104, 130. The second arm 158 also has an aperture in which a protrusion of the release tube 104 extends inwardly. When a force drives the release tube 104 toward the fusion cage 102, or away from the fusion cage 102 in some embodiments, the movement of the release tube 104 causes the protrusion 170 to move out of the aperture 169 and drive into the first arm 156, which causes the first arm to deflect to an inward position. As a result, the protrusions of the first arm 156 disengage from the fusion cage 102. The second arm 158 similarly disengages the fusion cage 102, and the fusion cage 102 can be removed from the inserter tube 130.

Figure 23:
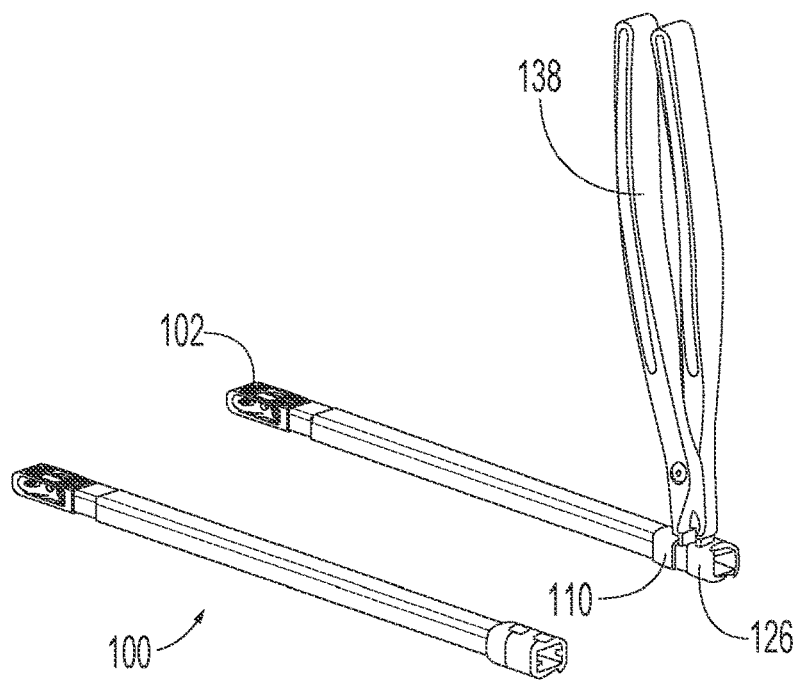
FIG. 23 is a perspective view of a delivery assembly with an inserter tube being removed from a release tube.
Figure 24:
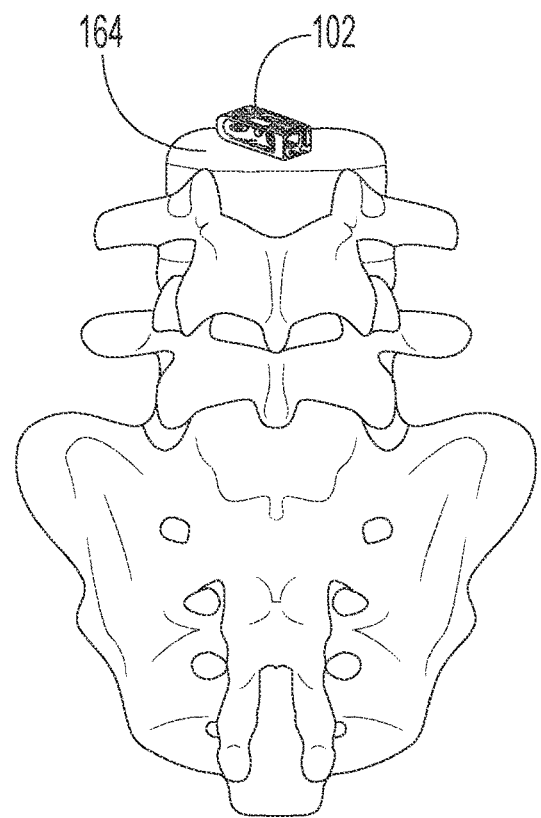
FIG. 24 is a perspective view of a fusion cage position in a spine.

Referring to FIGS. 23 and 24, perspective views of the delivery assembly 100 and the fusion cage 102 are provided, respectively. In FIG. 23, pliers 138 apply a force between the release collar 110 and the inserter collar 126 to drive the collars 110, 126 and their respective tubes apart. FIG. 24 shows the fusion cage 102 removed from the inserter tube and the delivery assembly, and the fusion cage 102 and the bone graft material positioned in a disc space 164 within a spinal column.

Figure 25:
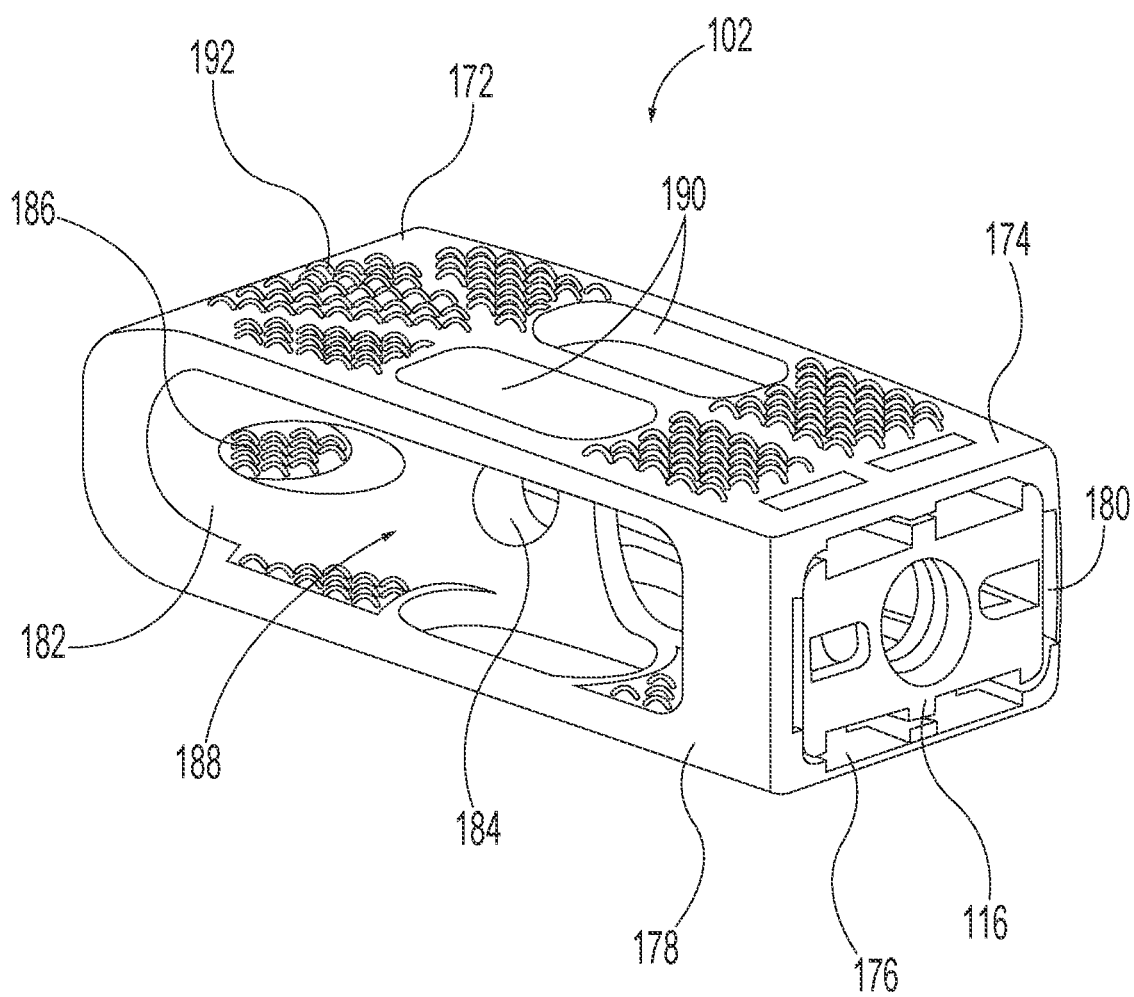
FIG. 25 is a perspective view of a fusion cage.

Referring to FIG. 25, a perspective view of a fusion cage 102 is provided. The fusion cage 102 has a body 172, which in this embodiment has a substantially rectangular shape. It will be appreciated that embodiments of the present disclosure encompass fusion cages 102 and related bodies 172 with a variety of shapes. The rectangular-shaped body 172 in FIG. 25 has a top side 174 and an opposing bottom side 176 as well as a left side 178 and an opposing right side 180. The fusion cage 102 has an opening at a proximal end of the body 172, and a cover plate 116 is positioned in this opening in FIG. 25. Prior to the installation of the cover plate 116, the delivery assembly delivers bone graft material through the opening and into the fusion cage 102.

Still referring to FIG. 25, the fusion cage 102 has a ramp 182 that extends between the top side 174 and the bottom side 176 of the body 172. A proximal end of the ramp 182 is positioned at midpoint or centerline between the left and right sides 178, 180 of the body 172. Then, as the ramp 182 extends to a distal end, the ramp 182 has one face that turns toward the left side 178 of the body 172 and has a right face that turns toward the right side 180 of the body 172. Thus, the incoming bone graft material contacts the ramp 182, which directs the bone graft material out of the left and right sides 178, 180 of the body 172 and into the disc space of the spinal column. The ramp 182 in this embodiment also has a retrieval aperture 184 located next to the proximal end of the ramp 182. If for some reason the fusion cage 102 needs to be moved within the disc space or completely removed from the disc space, a tool can secure to the retrieval aperture 184 to move or completely remove the fusion cage 102.

The fusion cage 102 has several apertures to direct the flow of bone graft material to desired locations within the disc space of the spinal column. The ramp 182 can comprise a forward aperture 186 through one face of the ramp 182 and another forward aperture through the other face of the ramp 182, which is not shown in FIG. 25. The forward apertures 186 direct bone graft material out of a distal end of the body 172. Next, the left side 178 has a side aperture 188 that is a single, continuous aperture 188 in this embodiment. The right side 180 also has a corresponding side aperture. The ramp 182 and ramp faces direct much of the bone graft material out of the side apertures 188. Each side aperture can be described as covering between 70-95% of the area of the respective side of the body 172. In various embodiments, each side aperture covers at least 80% of the respective side. The top side 174 of the body has two top apertures 190. The top apertures 190 can be described as covering between 5-40% of the area of the top side 174. In various embodiments, the top apertures 190 cover at least 5% of the area of the top side 174. The bottom side 176 also similar bottom apertures in a similar configuration as the top apertures 190.

The apertures of the fusion cage 102 can be sized relative to each other to direct more or less bone graft material out of certain apertures. Generally, the fusion cage 102 is positioned adjacent to the spinal cord within a disc space. Thus, each side aperture 188 covers a larger area than the top apertures, the bottom apertures, or the forward apertures. It can be important to fill voids above and below the fusion cage 102, and thus, each of the top apertures and bottom apertures cover a larger area than the forward aperture. As stated above, the fusion cage 102 can be positioned to one side of the spinal cord. Thus, it may be advantageous to eject more bone grant material through a larger left or right side aperture than the opposing aperture. The top apertures, bottom apertures, and forward apertures may also have different sized, asymmetric apertures to accommodate this aspect of bone graft delivery.

In addition, the fusion cage 102 can have one or more enhanced surfaces 192 positioned on the body 172. The enhanced surfaces 192 can be described as osseointegration areas that promote bonding with bone graft material and/or bone. The enhanced surfaces 192 each have a plurality of protrusions and a plurality of depressions to increase the surface area of the enhanced surfaces 192. In this embodiment, the enhanced surfaces 192 have a mesh shape. In various embodiments, the enhanced surfaces 192 have one or more pathways for bone graft material to travel from inside the fusion cage 102 to the disc space outside of the fusion cage 102.

Figure 26:
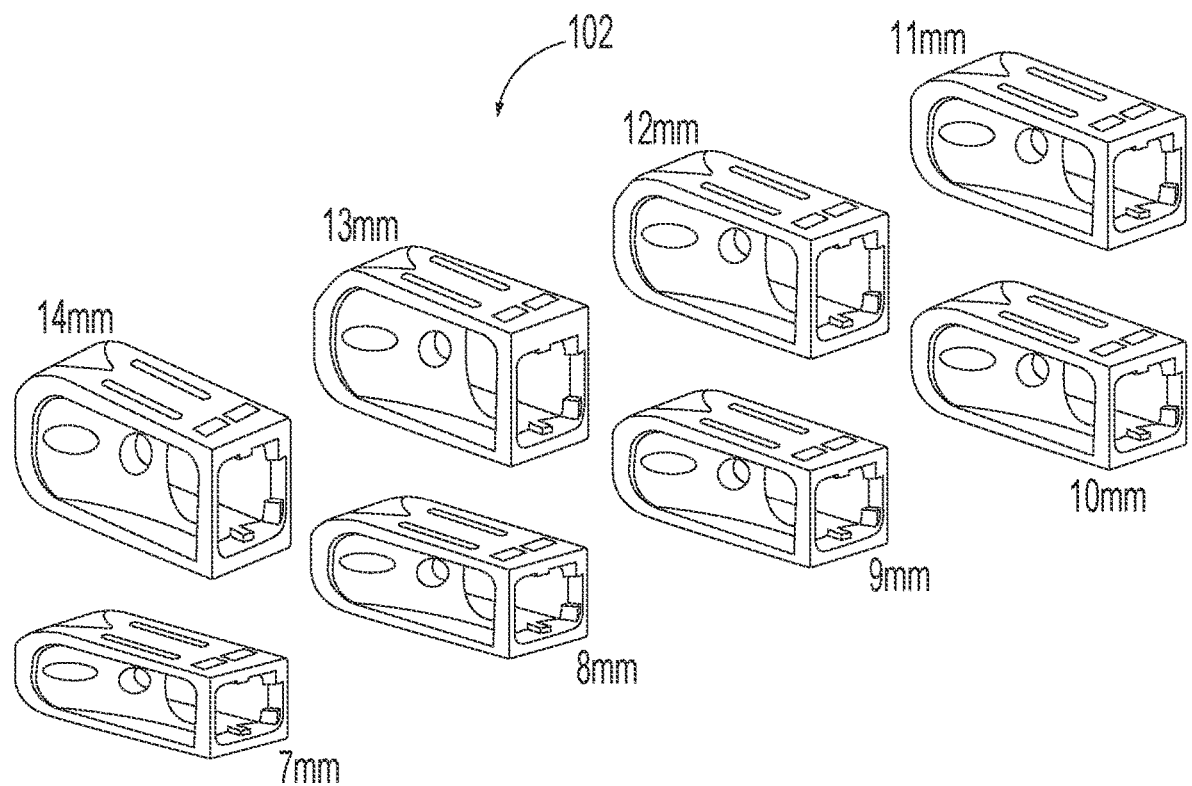
FIG. 26 is a perspective view of various embodiments of fusion cages.

Referring to FIG. 26, further perspective views of the fusion cage 102 are provided. These views show that the embodiments of the present disclosure encompass various sizes and configurations of fusion cages.

According to one embodiment, the present disclosure provides a bone graft delivery system, by which a hollow tube and/or plunger assembly may be prepared prior to opening a patient, thus minimizing the overall impact of the grafting aspect of a surgical implantation or other procedure. Moreover, the hollow may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device may either come with a prefilled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger and hollow tube cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

The integrated fusion cage with expandable cage feature provides a number of unique and innovative features not provided by conventional or traditional integrated fusion cages. For example, the integrated fusion cage with expandable cage feature of the disclosure is intentionally and deliberately designed to receive bone graft material (or any material suitable for use in surgical applications, as known to those skilled in the art) at its proximal end (i.e. the end generally facing the surgeon and/or the end opposite the end initially directed into a surgical site), such that the bone graft material flows into the fusion cage and also flows out from the fusion cage into the surgical site. Such features as the interior ramps of the fusion cage (e.g. located within the interior of the hollow tube, and/or on the front and/or rear blocks of the fusion cage) function to direct received bone graft material into the surgical site. Additionally, the features of the hollow tube and plunger wherein a greater volume of bone graft material may be reliably (e.g. not prone to blockage as is typical with most convention e.g. round hollow tubes or lumen systems) and readily delivered to a surgical site and/or a fusion cage are unique and not found in the prior art. Among other things, such features encourage improved surgical results by delivering more volume and coverage of bone graft material to the surgical site. Also, such features minimize gaps in bone graft coverage to include gaps between the fusion cage area and the surrounding surgical site. Also, the features of the one or more apertures of the fusion cage of the disclosure enable and encourage delivery of bone graft material, as received by the fusion cage, into the surrounding surgical site.

In contrast, conventional fusion cages, to include expandable fusion cages, do not provide such features and/or functions. For example, U.S. Pat. No. 8,852,242 to Morgenstern Lopez ("Lopez"), discloses a dilation introducer for orthopedic surgery for insertion of an intervertebral expandable fusion cage implant. The Lopez device does not allow receipt of bone graft material from its proximal end, or any end, in contrast to the disclosed fusion cage and fusion cage/bone graft delivery system. That is, the Lopez proximal end includes an array of components, all of which do not allow receipt of bone graft material. Furthermore, the Lopez device requires an elaborate array of components, e.g. upper side portion of the upper body portion and lower side portion of the lower body portion, which also block any egress of bone graft from the inside of the Lopez fusion cage once deployed. Also, the Lopez wedges occupy the entire interior of the cage; there are no ramps to direct graft from the interior to the disc space. In short, the Lopez design is not made with bone graft delivery in mind, and indeed, cannot function to accept let alone deliver bone graft. Additionally, suggestions provided in the Lopez disclosure to deliver bone graft to the surgical site would not provide the integrated and complete fusion cage and surgical site bone graft delivery of the disclosure, e.g. the Lopez slot of the Lopez lumen and funnel assembly at best provides limited delivery of bone graft material only before and after insertion of the Lopez fusion cage, and then only peripheral to the fusion cage. Also, it appears the Lopez device provides wedges and of similar if not identical interior ramp angles. In contrast, in certain embodiments of the present disclosure the interior wedged surfaces of the disclosure, i.e. front block ramp and rear block ramp, are not of the same configuration and/or shape, e.g. front block ramp is of a curved profile and rear block ramp is of a linear or straight-line profile. Among other things, the curved profile of the front block ramp urges egress of bone graft as received by the fusion cage.

In one embodiment of the fusion cage, no anti-torque structures or components are employed. In one embodiment of the disclosure, the lateral sides of the fusion cage are substantially open to, among other things, allow egress of bone graft material as received to the fusion cage. In one embodiment, the expansion screw is configured with a locking mechanism, such that the fusion cage may be locked at a set expansion state. In one embodiment, such a locking mechanism is provided through a toggle device operated at or on the installer/impactor handle.

In one embodiment, the front block ramp and rear block ramp are identical and/or symmetrical.

In addition, it is contemplated that some embodiments of the fusion cage can be configured to include side portions that project therefrom and facilitate the alignment, interconnection, and stability of the components of the fusion cage.

Furthermore, complementary structures can also include motion limiting portions that prevent expansion of the fusion cage beyond a certain height. This feature can also tend to ensure that the fusion cage is stable and does not disassemble during use.

In some embodiments, the expansion screw can facilitate expansion of the fusion cage through rotation, longitudinal contract of a pin, or other mechanisms. The expansion screw can also facilitate expansion through longitudinal contraction of an actuator shaft as proximal and distal collars disposed on inner and outer sleeves move closer to each other to in turn move the proximal and distal wedged block members closer together. It is contemplated that in other embodiments, at least a portion of the actuator shaft can be axially fixed relative to one of the proximal and distal wedge block members with the actuator shaft being operative to move the other one of the proximal and distal wedge members via rotational movement or longitudinal contraction of the pin.

Further, in embodiments wherein the engagement screw is threaded, it is contemplated that the actuator shaft can be configured to bring the proximal and distal wedged block members closer together at different rates. In such embodiments, the fusion cage could be expanded to a V-configuration or wedged shape. For example, the actuator shaft can comprise a variable pitch thread that causes longitudinal advancement of the distal and proximal wedged block members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, an upper plate can be configured to include anti-torque structures. The anti-torque structures can interact with at least a portion of a deployment tool during deployment of the fusion cage implant to ensure that the implant maintains its desired orientation. For example, when the implant is being deployed and a rotational force is exerted on the actuator shaft, the anti-torque structures can be engaged by a non-rotating structure of the deployment tool to maintain the rotational orientation of the implant while the actuator shaft is rotated. The anti-torque structures can comprise one or more inwardly extending holes or indentations on the rear wedged block member. However, the anti-torque structures can also comprise one or more outwardly extending structures.

According to yet other embodiments, the fusion cage can be configured to include one or more additional apertures to facilitate osseointegration of the fusion cage within the intervertebral space. The fusion cage may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the fusion cage and can be inserted into the disc space or inserted along with the fusion cage. The apertures can facilitate circulation and bone growth throughout the intervertebral space and through the implant. In such implementations, the apertures can thereby allow bone growth through the implant and integration of the implant with the surrounding materials.

In one embodiment, the fusion cage comprises an expandable cage configured to move a first surface vertically from a second surface by rotation of at least one screw that rotates without moving transversely with respect to either said first or second surface, said first plate and second plate having perimeters that overlap with each other in a vertical direction and that move along a parallel line upon rotation of the screw.

In one embodiment, the fusion cage is stackable by any means known to those skilled in the art. For example, each upper plate may be fitted with one or more notches on the lateral edges configured to fit with one or more protrusions on each lower plate.

According to various embodiments of the present disclosure, one aspect of the disclosure is to provide a graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, crosssections of an oval shape, or those that are approximately rectangular and have rounded corners or edges, or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

In embodiments, a distal end of the hollow tubular member may be at least partially closed, and/or may have a small aperture associated with the lumen. This partial closure and/or small aperture may help to create a consistent and clean break between bone graft material that has been ejected from the hollow tubular member and bone graft material held within the hollow tubular member.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

The plunger may be inserted into the hollow tube such that the horizontal face is substantially planar with the opening at the second end of the hollow tube. As described above, the geometry of plunger is such that it fits snugly or tightly in the interior of the hollow tube. This configuration is such that the sloped or curved surface of the hollow tube is substantially congruent to the sloped or curved surface, thereby allowing the plunger to be inserted into the hollow tube and allowing substantially all of bone graft material which is placed into the hollow tube to be ejected by the user.

Another embodiment for the bone graft insertion device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunger along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360-degree rotation of the plunger equates to 5 cc of bone graft material delivered to the bone graft site.

In embodiments of bone graft insertion devices and systems of the present disclosure, a spinal implant adapted for interconnection and use with the bone graft insertion device and/or included in the bone graft insertion system may comprise a covering or mesh, such as a biodegradable polymer mesh, and/or may be detachably interconnected to the bone graft insertion device by means of, e.g., a hook attachment mechanism, a screw attachment mechanism, a mechanical attachment mechanism, a suture attachment mechanism, a wrap attachment mechanism, and/or an adhesive attachment mechanism. Examples of spinal implants of this type, suitable for use in the present disclosure, include but are not limited to the spinal implants described in U.S. Pat. No. 10,028,837, issued Jul. 24, 2018 to Wei et al., the entirety of which is incorporated herein by reference.

In embodiments of bone graft insertion devices and systems of the present disclosure, a spinal implant adapted for interconnection and use with the bone graft insertion device and/or included in the bone graft insertion system may comprise an expandable portion adapted to expand or inflate when filled with bone graft or other material, and/or may be detachably interconnected to the bone graft insertion device by means of, e.g., an adhesive. Examples of spinal implants of this type, suitable for use in the present disclosure, include but are not limited to the spinal implants described in U.S. Pat. No. 9,925,060, issued Mar. 27, 2018 to DiMauro et al., the entirety of which is incorporated herein by reference.

In embodiments of bone graft insertion devices and systems of the present disclosure, a spinal implant adapted for interconnection and use with the bone graft insertion device and/or included in the bone graft insertion system may comprise any one or more of a nucleus replacement device, a nucleus augmentation device, an anulus augmentation device, an anulus replacement device, a drug carrier device, a carrier device seeded with living cells, a device that stimulates or supports fusion of the surrounding vertebra, and/or a membrane that prevents flow of a material through a defect in a disc of the patient; the implant may be wholly or partially rigid or wholly or partially flexible. Examples of spinal implants of this type, suitable for use in the present disclosure, include but are not limited to the spinal implants described in U.S. Pat. No. 9,333,087, issued May 10, 2016 to Lambrecht, the entirety of which is incorporated herein by reference.

In embodiments of bone graft insertion devices and systems of the present disclosure, a spinal implant adapted for interconnection and use with the bone graft insertion device and/or included in the bone graft insertion system may comprise any one or more of a plate, spacer, rod, or other stabilization device, and in particular may comprise an expandable or non-expandable spacer having an opening for receiving graft material therein, and/or may (but need not) be detachably interconnected to the bone graft insertion device by means of, e.g., a threaded attachment. Examples of spinal implants of this type, suitable for use in the present disclosure, include but are not limited to the spinal implants described in U.S. Pat. No. 9,827,113, issued Nov. 28, 2017 to Klimek et al., the entirety of which is incorporated herein by reference.

In embodiments of bone graft insertion devices and systems of the present disclosure, a spinal implant adapted for interconnection and use with the bone graft insertion device and/or included in the bone graft insertion system may comprise a body portion, a carriage portion, a deployment assembly, and an expandable portion, and/or may be detachably interconnected to the bone graft insertion device by means of, e.g., one or more detents and holes or apertures for receiving the detents. Examples of spinal implants of this type, suitable for use in the present disclosure, include but are not limited to the spinal implants described in U.S. Pat. No. 10,076,421, issued Sep. 18, 2018 to Dewey, the entirety of which is incorporated herein by reference.

In embodiments of bone graft insertion devices and systems of the present disclosure, a spinal implant adapted for interconnection and use with the bone graft insertion device and/or included in the bone graft insertion system may comprise a gear and a threaded shaft, whereby rotation of the gear engages the threaded shaft to expand the implant such that the implant can be inserted in a collapsed configuration and expanded in situ, and/or may (but need not) be detachably interconnected to the bone graft insertion device by means of, e.g., screws, clips, hooks, and/or clamps. Examples of spinal implants of this type, suitable for use in the present disclosure, include but are not limited to the spinal implants described in U.S. Pat. No. 10,226,358, issued Mar. 12, 2019 to Glerum, the entirety of which is incorporated herein by reference.

In embodiments of bone graft insertion devices and systems of the present disclosure, a spinal implant adapted for interconnection and use with the bone graft insertion device and/or included in the bone graft insertion system may comprise a plurality of chambers, each of the chambers being configured to receive bone graft material, and/or may include means allowing a surgeon or other user to select a chamber or portion of the interior of the implant into which bone graft material is delivered. Examples of spinal implants of this type, suitable for use in the present disclosure, include but are not limited to the spinal implants described in U.S. Pat. No. 9,545,282, issued Jan. 17, 2017 to Mathur et al., the entirety of which is incorporated herein by reference.

It is to be expressly understood that spinal implant suitable for use as part of, or in conjunction with, the devices, methods, and systems of the present disclosure are not limited to the examples described above, and that any type of spinal implant appropriate for a given application may be detachably interconnected to a bone graft delivery device and used in the 5 methods and systems of the present disclosure. By way of non-limiting example, anterior and/or lateral interbody spinal implants, including but not limited to implants available under the SeaSpine Redondo™, Regatta®, and Vu a·POD™ product lines, may be detachably interconnected to a bone graft delivery device by any suitable means and used in the practice of the present disclosure. By way of further non-limiting example, posterior interbody spinal 10 implants, including but not limited to implants available under the SeaSpine Hollywood™, Hollywood™ VI, Pacifica™, Steerable Interbody, Ventura™, and Vu L·POD™ product lines, may be detachably interconnected to a bone graft delivery device by any suitable means and used in the practice of the present disclosure. These and other spinal implants suitable for use in the present disclosure are described in U.S. Pat. Nos. 7,799,083, 7,976,549, 7,988,695, 8,100,972, 8,142,508, 8,292,958, 8,366,774, 8,409,290, 8,506,636, 8,545,562, 8,673,012, 8,864,829, and 9,522,069, the entirety of each of which is incorporated herein by reference.

While various embodiment of the present disclosure have been described in detail, it is apparent that modifications and alterations of those embodiments will occur to those skilled in the art. However, it is to be expressly understood that such modifications and alterations are 20 within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred 30 embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A kit for bone graft delivery comprising:
   an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening;
   a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge; and
   an inserter tube having a rod configured to rotatably engage the rotating wedge and move the tabs so as to secure the cover plate to the at least one of the plurality of sidewalls to cover the delivery opening,
   wherein the cover plate is configured to be entirely contained within the delivery opening of the implant, and whereby rotation of the rotating wedge causes the tabs to extend outwardly and securely engage the inside borders of the delivery opening to secure the cover plate to the first sidewall, and
   wherein the first sidewall includes first and second protrusions and each of the tabs includes a recess configured to receive a respective one of the first and second protrusions therein, to thereby secure the cover plate to the first sidewall.

2. The kit of claim 1, wherein the rotating wedge includes an outer surface and at least one protrusion extending therefrom that is configured to drive one of the tabs to extend outwardly.

3. The kit of claim 2, wherein the tabs each include a recess configured to receive a respective protrusion of the at least one protrusion of the rotating wedge therein, to maintain each of the tabs in the outwardly extended position.

4. The kit of claim 1, wherein the tabs are push-out leaf tabs.

5. The kit of claim 1, wherein the implant is a cage-like implant.

6. A kit for bone graft delivery comprising:
   an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening; and
   a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge;
   wherein the cover plate is configured to be entirely contained within the delivery opening of the implant, and whereby rotation of the rotating wedge causes the tabs to extend outwardly and securely engage the inside borders of the delivery opening to secure the cover plate to the first sidewall; and
   wherein the first sidewall includes first and second protrusions and each of the tabs includes a recess configured to receive a respective one of the first and second protrusions therein, to thereby secure the cover plate to the first sidewall.

7. The kit of claim 6, wherein the rotating wedge includes an outer surface and at least one protrusion extending therefrom that is configured to drive one of the tabs to extend outwardly.

8. The kit of claim 7, wherein the tabs each include a recess configured to receive a respective protrusion of the at least one protrusion of the rotating wedge therein, to maintain each of the tabs in the outwardly extended position.

9. The kit of claim 6, wherein the tabs are push-out leaf tabs.

10. The kit of claim 6, wherein the implant is a cage-like implant.

11. The kit of claim 6, further comprising an inserter tube having a rod configured to rotatably engage the rotating wedge and move the tabs so as to secure the cover plate to the at least one of the plurality of sidewalls to cover the delivery opening.

12. A kit for bone graft delivery comprising:
   an implant having a top wall, a bottom wall opposite the top wall, and a plurality of sidewalls extending between the top and bottom walls to define an interior space, wherein a first sidewall of the plurality of sidewalls has a delivery opening that is continuous with the interior space, such that the first sidewall defines inside borders of the delivery opening;
   a cover plate configured to be secured to the implant within the delivery opening of the first sidewall, the cover plate including: an exterior surface and an interior surface opposite the exterior surface, wherein the interior surface includes a rotating wedge and tabs, wherein the tabs are operably connected to the rotating wedge; and
   an inserter tube having a rod configured to rotatably engage the rotating wedge and move the tabs so as to secure the cover plate to the at least one of the plurality of sidewalls to cover the delivery opening;
   wherein the cover plate is configured to be entirely contained within the delivery opening of the implant;
   whereby rotation of the rotating wedge causes the tabs to extend outwardly and securely engage the inside borders of the delivery opening to secure the cover plate to the first sidewall; and
   wherein the first sidewall includes first and second protrusions and each of the tabs includes a recess configured to receive a respective one of the first and second protrusions therein, to thereby secure the cover plate to the first sidewall.

13. The kit of claim 12, wherein the rotating wedge includes an outer surface and at least one protrusion extending therefrom that is configured to drive one of the tabs to extend outwardly.

14. The kit of claim 13, wherein the tabs each include a recess configured to receive a respective protrusion of the at least one protrusion of the rotating wedge therein, to maintain each of the tabs in the outwardly extended position.

15. The kit of claim 12, wherein the tabs are push-out leaf tabs.

16. The kit of claim 12, wherein the implant is a cage-like implant.

* * * * *